US008100005B2

(12) United States Patent
Fane et al.

(10) Patent No.: US 8,100,005 B2
(45) Date of Patent: Jan. 24, 2012

(54) PERMEATE FLOW DISTRIBUTION MEASUREMENT IN A MEMBRANE FILTRATION SYSTEM

(75) Inventors: Anthony G. Fane, Grays Point (AU); Filicia Wicaksana, Singapore (SG); Adrian Wing-Keung Law, Singapore (SG)

(73) Assignee: Nanyang Technological University, Singapore (SG)

( * ) Notice: Subject to any disclaimer, the term of this patent is extended or adjusted under 35 U.S.C. 154(b) by 491 days.

(21) Appl. No.: 12/415,940

(22) Filed: Mar. 31, 2009

(65) Prior Publication Data

US 2010/0242575 A1    Sep. 30, 2010

(51) Int. Cl.
*G01F 7/00* (2006.01)
(52) U.S. Cl. .................................................. 73/195
(58) Field of Classification Search .............. 73/195, 73/196
See application file for complete search history.

(56) References Cited

U.S. PATENT DOCUMENTS 4,581,930 A * 4/1986 Komons ............... 73/204.17
2010/0282676 A1* 11/2010 Liberman et al. ........... 210/636

FOREIGN PATENT DOCUMENTS

WO         2007/108977        9/2007
WO     WO 2007108977 A2 *   9/2007

OTHER PUBLICATIONS

Boelhouwer et al., "Particle-liquid heat transfer in trickle-bed reactors" Chemical Engineering Science 56: 1181-1187, 2001.
Chang et al., "Observation of flow characteristics in a hollow fiber lumen using non-invasive X-ray microimaging (XMI)" Journal of Membrane Science 304: 181-189, 2007.
Elvery et al., "Directional Sensitivity of wall mounted hot-film gauges" Meas. Sci. Technol. 7: 1410-1417, 1996.
Le-Clech et al., "The application of constant temperature anemometry to membrane processes" Journal of Membrane Science 284: 416-423, 2006.
Meunier et al., "Realization and simulation of wall shear stress integrated sensors" Microelectronics Journal 34: 1129-1136, 2003.
Michiyoshi et al., "Turbulence In Two-Phase Bubbly Flow" Nuclear Engineering and Design 95: 253-267, 1986.
Soira et al., "A Study of the Three-Term Hot-Wire System Equation and Analog Linearization Based on It" Experimental Thermal and Fluid Science 3: 346-353, 1990.
Oever, "MBR focus: is submerged best?" Filtration + Separation 42(5): pp. 24, Jun. 2005, 4 pages.
Wernersson et al., "Turbulence characteristics in turbine-agitated tanks of different sizes and geometries" Chemical Engineering Journal 72: 97-107, 1999.
Yeo et al., "Factors affecting the performance of a submerged hollow fiber bundle" Journal of Membrane Science 280: 969-982, 2006.
Probes for Hot-wire Anemomemtry, Dantec Dynamics A/S, catalog, 2005, publication No. 238-1, 25 pages.
URECA Year Book 2007, Proceedings of the URECA @ NTU, Nanyang Technological University, 2006-2007, published Apr. 2008, 74 pages.

* cited by examiner

*Primary Examiner* — Hezron E Williams
*Assistant Examiner* — Nathaniel Kolb
(74) *Attorney, Agent, or Firm* — Seed IP Law Group PLLC

(57) ABSTRACT

The present invention refers to a flow distribution measuring system comprising a sensor matrix adapted to measure the flow distribution of permeate passing through a membrane filtration arrangement and also refers to a cap comprising such a sensor matrix; wherein the cap is adapted to be affixed to a membrane filtration arrangement. The present invention further refers to methods of using the flow distribution measuring system and the cap.

32 Claims, 17 Drawing Sheets

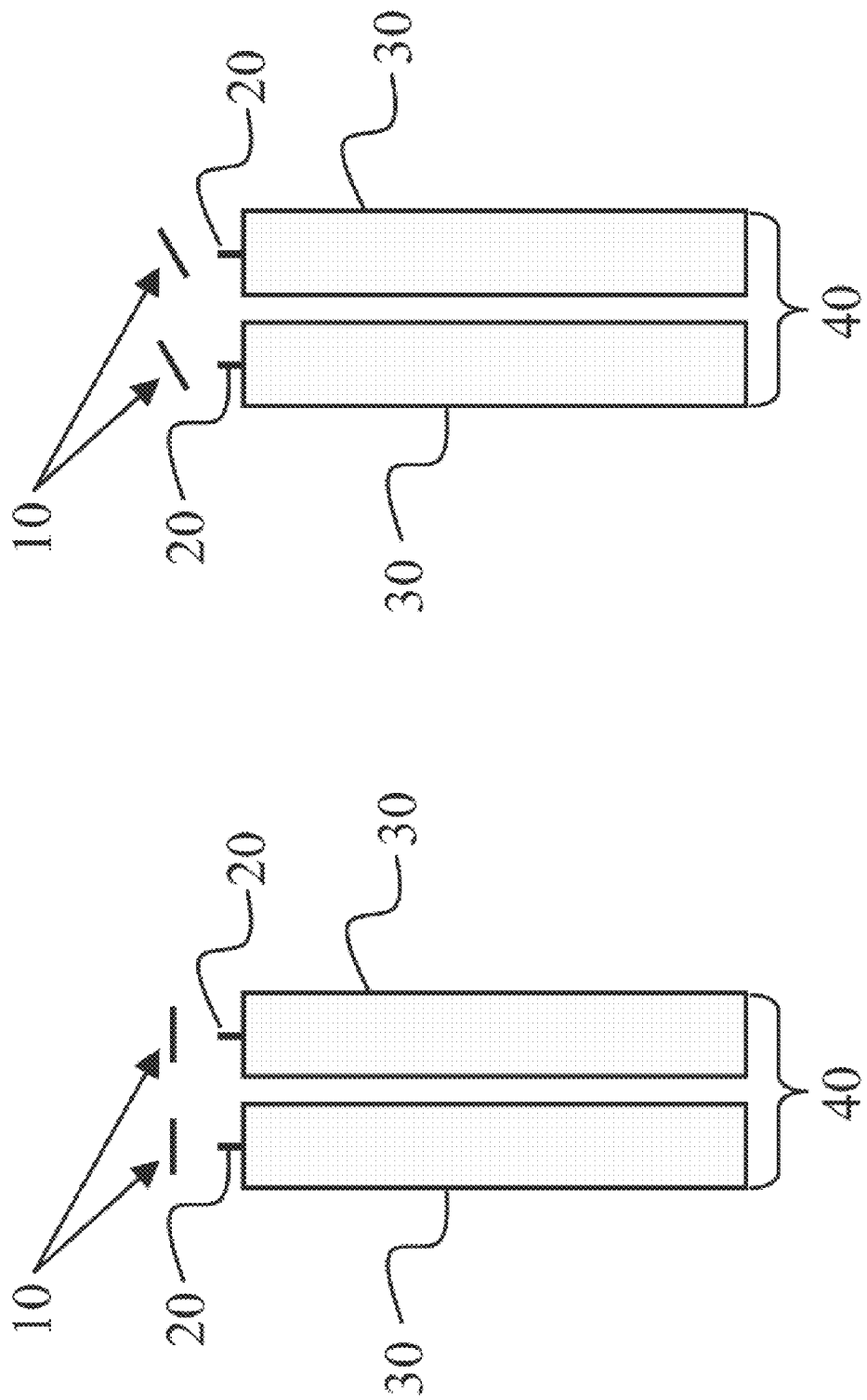

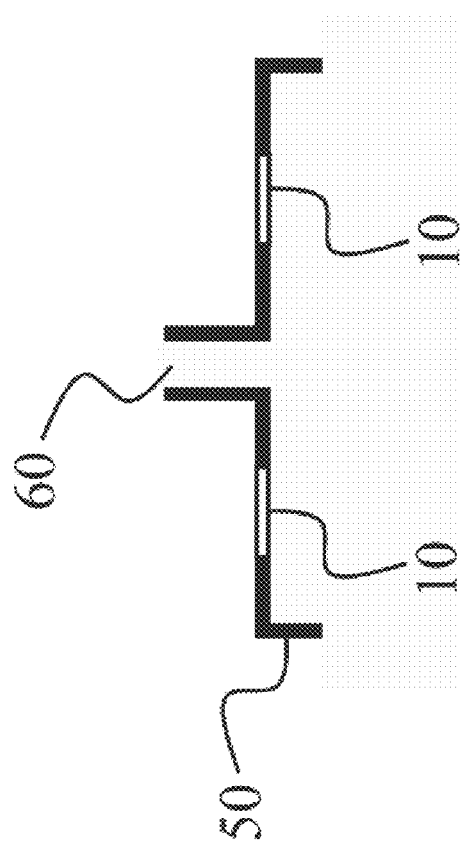
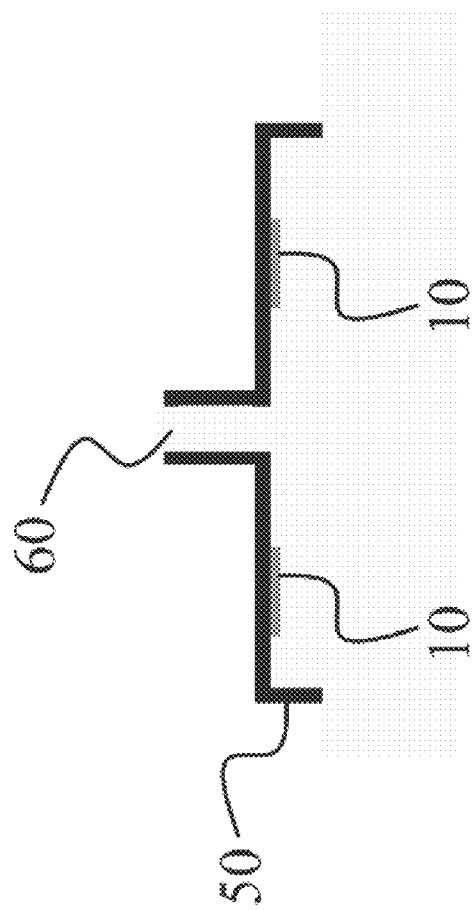

Fig. 8
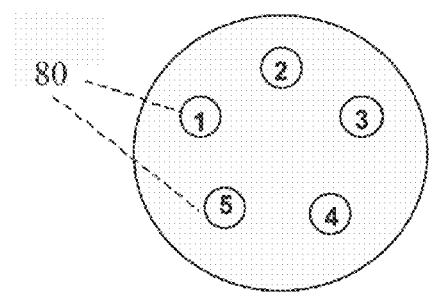
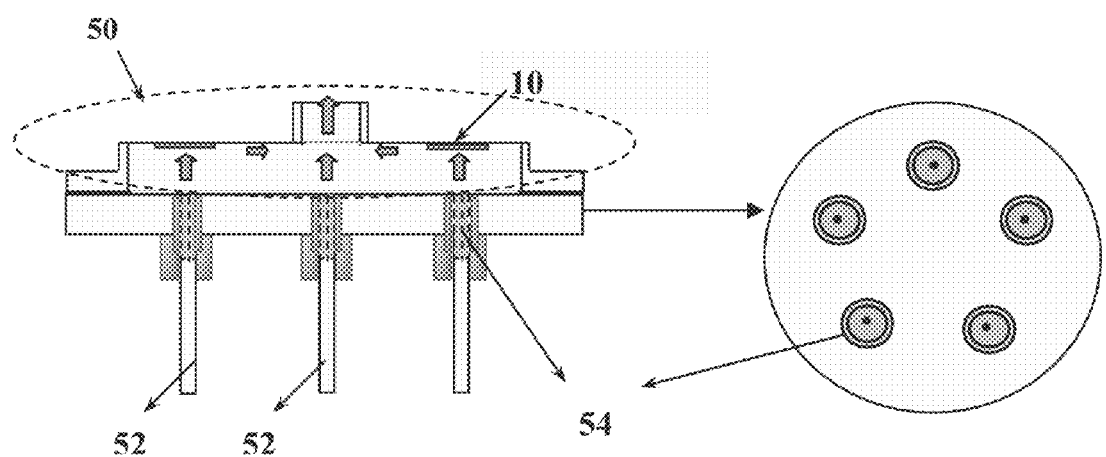
Fig. 9A            Fig. 9B

PERMEATE FLOW DISTRIBUTION MEASUREMENT IN A MEMBRANE FILTRATION SYSTEM

BACKGROUND

1. Technical Field

The present invention refers to a measuring system for measuring the flow distribution of permeates passing through a filtration membrane and to methods for using such a measuring system.

2. Description of the Related Art

One of the uses of membrane technology lies in the application of membrane bioreactors (MBR) which are used as one component in wastewater treatment plants.

The membrane bioreactor (MBR) as part of a wastewater treatment plant is a compact-built purification system combining the biological degradation step with a membrane separation step. The aqueous part of wastewater fed into an MBR passes through the membrane pores, thus separating the liquid from particulate matters. The liquid that passes through the pores of the membrane is called permeate. This permeate is afterwards discharged (then it is also called "effluent"), subjected to further cleaning treatment or re-used as particle free effluent in wastewater treatment plant.

In membrane-based separation systems, in particular in submerged membrane systems where membranes are subjected to a high biomass concentration of activated sludge, fouling is a major obstacle.

In general, membrane fouling can be defined as the accumulation of particles/substances on the surface of a membrane. Thus, the term membrane fouling comprehensively refers to a series of phenomenon which can comprise of pore adsorption, pore blocking or clogging, gel formation or cake formation.

Fouling can be reversible or irreversible depending on how strong the particles attached to the membrane surface. Reversible fouling can be overcome by periodic backwashing. Irreversible fouling is generally caused by strong particle attachment and this type of fouling requires intense chemical cleaning or membrane replacement.

Since submerged membranes are generally operated under constant flux, a commonly employed measure to indicate membrane fouling under this operating mode is the upsurge of overall transmembrane pressure. However, this parameter has been found to be insensitive for indicating an early state of fouling. Therefore, an early warning of fouling is essential to optimize the system performance. When fouling is insignificant, the permeate distribution is likely to be uniform. As the fouling progresses, a mal-distribution of permeate flow may occur. Thus, it is an object of the present invention to provide techniques which can facilitate the detection of incipient fouling.

BRIEF SUMMARY OF THE INVENTION

The present invention refers in a first aspect to a flow distribution measuring system having:

a sensor matrix adapted to measure the flow distribution of permeate passing through a membrane filtration arrangement;

wherein the sensor matrix comprises at least two sensors measuring permeate velocity;

wherein the membrane filtration arrangement comprises at least two membrane filtration elements each comprising an outlet for the permeate;

wherein at the outlet of each of the at least two membrane filtration elements one of the sensors of the sensor matrix is located for measuring the permeate velocity at the outlet.

In another aspect, the present invention refers to a flow distribution measuring system comprising:

a sensor matrix adapted to measure the flow distribution of permeate passing through a hollow fiber filtration membrane;

wherein the hollow fiber filtration membrane comprises multiple hollow fibers each having an outlet for permeate;

wherein the sensor matrix comprises at least two sensors measuring permeate velocity; and wherein the at least two sensors are arranged above the multiple outlets of the multiple hollow fibers.

In another aspect, the present invention refers to a cap having a sensor matrix comprising sensors measuring the velocity of permeate exiting through outlets of at least two membrane filtration elements of a membrane filtration arrangement;

wherein the cap is adapted to be affixed on a membrane filtration arrangement wherein the cap comprises an outlet through which the permeate can exit the cap.

In a further aspect, the present invention refers to a cap comprising a sensor matrix which comprises sensors measuring the velocity of permeate exiting through multiple outlets of hollow fibers of a hollow fiber filtration membrane; wherein the cap is adapted to be affixed on the hollow fiber filtration membrane; and wherein the cap comprises an outlet through which the permeate exits the cap.

In a further aspect, the present invention refers to a method of measuring the flow distribution in a membrane filtration arrangement including:

providing a flow distribution measuring system of the present invention; and measuring the individual permeate flow velocity at each outlet of the membrane filtration arrangement to determine the flow distribution pattern in the membrane filtration arrangement In another aspect, the present invention refers to a method of measuring the flow distribution in a hollow fiber filtration membrane; comprising:

providing a flow distribution measuring system of the present invention including a hollow fiber filtration membrane; and measuring the permeate flow velocity above the outlets of the multiple hollow fibers of the hollow fiber filtration membrane to determine the flow distribution pattern in the hollow fiber filtration membrane.

In a further aspect, the present invention refers to a method of measuring the flow distribution in a membrane filtration arrangement including:

providing a cap of the present invention;

affixing the cap to an end of a membrane filtration arrangement, wherein the end comprises outlets of membrane filtration elements forming part of the membrane filtration arrangement;

measuring the individual permeate flow velocity at each outlet of the membrane filtration arrangement to determine the flow distribution pattern in the membrane filtration arrangement.

In a further aspect, the present invention refers to a method of measuring the flow distribution in a hollow fiber filtration membrane comprising:

providing a cap of the present invention;

affixing the cap to an end of the hollow fiber filtration membrane, wherein the end comprises the outlets of the multiple hollow fibers comprised in the hollow fiber filtration membrane; and measuring the permeate flow velocity above the outlets of the hollow fibers of the hollow fiber filtration membrane to determine the flow distribution pattern in the hollow fiber filtration membrane.

BRIEF DESCRIPTION OF THE SEVERAL VIEWS OF THE DRAWINGS

The invention will be better understood with reference to the detailed description when considered in conjunction with the non-limiting examples and the accompanying drawings, in which:

FIGS. 1A and 1B show the setup of a flow distribution measuring system including sensors 10, a membrane filtration arrangement 40 with membrane filtration elements 30 wherein each of the membrane filtration elements comprises an outlet 20. Compared to the embodiment shown in FIG. 1A, the sensors in FIG. 1B are arranged in an angle of 30° to the outlets 20 of the membrane filtration elements 30.

FIG. 2A shows two flat sheet membrane filtration elements 30 while FIG. 2B shows four hollow fiber membrane filtration elements 30 wherein each of the elements in FIG. 2B comprises a bundle of hollow fibers. FIG. 2C also shows a cap 71 in which the sensor matrix is located and the outlet 73 of this cap 71. Other than in the embodiments illustrated in FIGS. 1A, 1B, each sensor measures not only the permeate flow at one outlet of a membrane filtration element of a membrane filtration arrangement but the combined permeate exiting through several outlets of different hollow fibers of a hollow fiber filtration membrane.

FIGS. 3A and 3B illustrate two different examples of a cap which can be affixed to the end of a membrane filtration arrangement or a hollow fiber filtration membrane illustrated in FIG. 2C. The caps 50 comprise an outlet 60 and sensors 10 wherein the sensors in FIG. 3A are fixed, such as by gluing, to the cap 50 while in FIG. 3B the sensors are embedded in the cap 50.

FIG. 6 illustrates the setup of an experimental flow distribution measurement system including the StreamLine data logging system 33 for evaluation of the data obtained from the sensors 10 located on the inner side of the cap (FIGS. 6B and 6C). FIG. 6B shows a bottom view of the cap while

FIG. 8 shows a top view into an exemplary membrane filtration arrangement comprising five membrane filtration elements 80 (numbered 1 to 5). Each of the five membrane filtration elements is a hollow fiber filtration membrane comprised of a bundle of hollow fibers.

FIG. 9A illustrates the permeate flow (arrows) in a cap which can be fixed to a membrane filtration arrangement. The outlet 52 feeds permeate from the membrane filtration element to the cap including the sensors 10. Due to the side sectional view only two of the five sensors 10 can be seen. FIG. 9B shows the top view onto the membrane filtration arrangement comprising five membrane filtration elements. The center black dot indicates outlet tubings connected to the outlet 52. The outlet tubings have a narrower diameter so that the velocity of the permeate passing through them increases to reach the minimum measurement limit of the velocity sensors 10.

DETAILED DESCRIPTION

In a first embodiment, the present invention refers to a flow distribution measuring system comprising a sensor matrix adapted to measure the flow distribution of permeate flow passing through a membrane filtration arrangement;

wherein the sensor matrix comprises at least two sensors measuring permeate velocity;

wherein the membrane filtration arrangement comprises at least two membrane filtration elements each comprising an outlet for the permeate;

wherein at the outlet of each of the at least two membrane filtration elements one of the sensors of the sensor matrix is located for measuring the permeate velocity at the outlet.

The use of a sensor matrix instead of single sensors permits the measurement of permeate flow at various outlets of a membrane filtration arrangement. Hence, simultaneous and continuous measurement of the permeate flow distribution becomes more practical and reliable since multiple sensors can be installed.

This online (real-time) monitoring system provides knowledge of fouling distribution among multiple membrane filtration elements of a membrane filtration arrangement during filtration, thus allowing an optimization of the membrane filtration process by detecting incipient fouling in single elements of a membrane filtration arrangement. The system referred to herein also facilitates detection of incipient blocking. In general, membrane blocking refers to the accumulation of cake, e.g., within a hollow fiber membrane (module) (i.e., in the gap between hollow fibers), while fouling means the accumulation of particles on the membrane surface or inside the membrane pores. Due to the possibility to determine the membrane filtration element of the arrangement most affected by fouling or blocking, this system allows to decide which element of the arrangement requires replacement. Overall costs can be reduced by selective treating or replacing of single membrane filtration elements rather than treating or replacing the whole membrane filtration arrangement.

A membrane filtration arrangement comprises multiple membrane filtration elements. Examples for membrane filtration elements include, but are not limited to a flat sheet filtration membrane also called flat sheet filtration module or a hollow fiber filtration membrane also called hollow fiber filtration module.

A hollow fiber filtration membrane consists of multiple hollow fibers arranged in a bundle or a curtain-like structure. Each fiber functions like an independent filtration membrane and comprises at its end an opening or outlet through which permeate exits which has been obtained by filtering liquid through the pores in the wall of the hollow fiber.

Figure 2C:
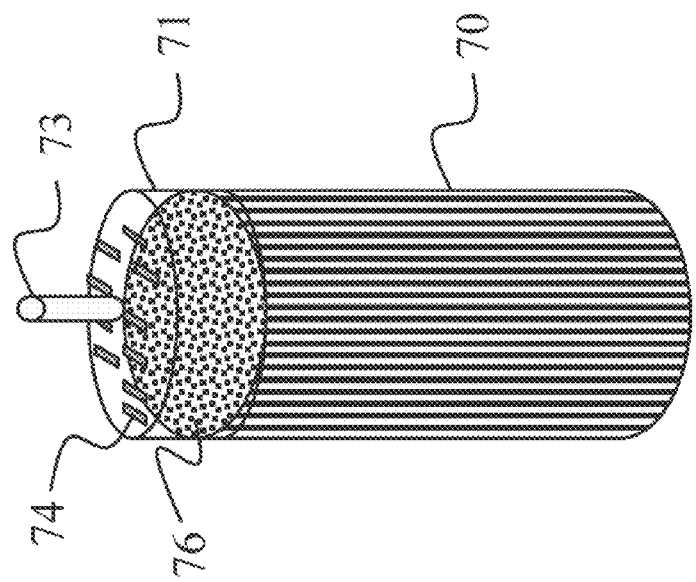
FIG. 2C shows another embodiment of the present invention in which the sensors 74 of a sensor matrix are located directly above the outlets 76 (small black dots) of multiple hollow fibers (shown as black stripes in the hollow fiber filtration membrane 70) which form part of a hollow fiber filtration membrane 70.
Figure 2B:
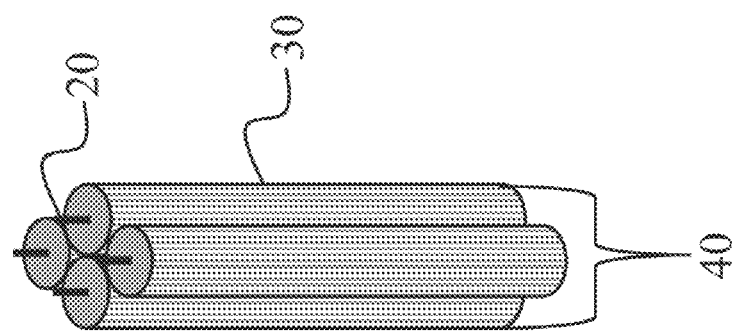
FIGS. 2A and 2B illustrate two different membrane filtration arrangements 40 including two different types of membrane filtration elements 30.
Figure 27:
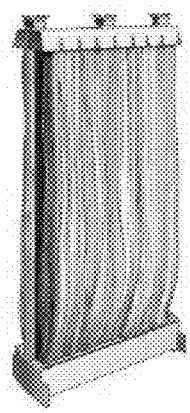
FIG. 27 shows an example of a curtain-like hollow fiber filtration membrane (ZENON Environmental Inc., GE-membranes).

A curtain-like hollow fiber filtration membrane comprises multiple hollow fibers arranged next to each other to form a curtain of hollow fibers rather than a bundle as illustrated in FIG. 2B. An example for a curtain-like module is illustrated in FIG. 27 (ZENON Environmental Inc., GE membranes).

FIG. 2B illustrates an example of a membrane filtration arrangement 40 comprised of four membrane filtration elements 30 each having an outlet 20 through which permeate can be extracted. Each of these elements 30 comprises a bundle of hollow fibers through which water is filtered. Another example for a membrane filtration element comprising hollow fibers is illustrated in FIG. 8. FIG. 8 shows a membrane filtration arrangement comprising five membrane filtration elements (numbered 1 to 5) of which each comprises a bundle of hollow fibers.

Figure 2A:
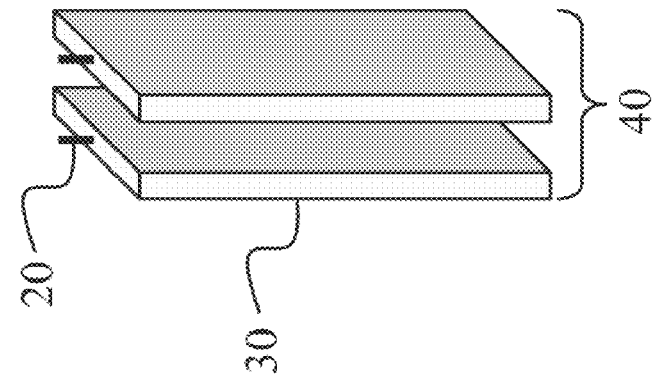

Another example of a membrane filtration element is a flat sheet membrane. Flat sheet filtration membranes are available in rectangles, squares, or pre-cut to fit the process filtration units used. An example for a flat sheet membrane filtration element is shown in FIG. 2A. FIG. 2A illustrates two flat sheet membrane filtration elements 30 having an outlet 20 and forming a membrane filtration arrangement 40. A flat sheet membrane filtration arrangement can comprise multiple flat sheet membrane filtration elements 30.

The membranes used in a membrane filtration element can be membranes used for reverse osmosis, nanofiltration, ultrafiltration or microfiltration. These filtration processes are not fundamentally different from each other, except in terms of the size of the molecules they retain.

Ultrafiltration is a membrane separation technique used to separate extremely small particles (in the size range of 20-1000 angstrom (up to 0.1 micron)) and dissolved molecules in fluids. The retention properties of ultrafiltration membranes are expressed as Molecular Weight cut-off (MWCO). This value refers to the approximate molecular weight (MW) of a dilute globular solute (i.e., a typical protein) which is 90% retained by the membrane. In general the pore size of the membranes used for ultrafiltration is around 0.01 μm. For nanofiltration processes the pore size of the membranes is around 0.001 μm. Microfiltration is a filtration process which removes contaminants from a fluid by passage through a microporous membrane. A typical microfiltration membrane pore size range is 0.1 to 10 μm. Reverse osmosis filters have in general a pore size around 0.0001 μm, i.e., after water passes through a reverse osmosis membrane, the water is essentially pure water. Reverse osmosis is used to obtain drinking water from salt containing water, such as sea water, by separating the monovalent ions from the salt containing water, i.e., it desalinates, e.g., sea water. It should also be noted that the separation size ranges of the above processes can partly overlap. In one embodiment, the flow distribution measuring system measures the flow distribution of at least two or multiple membrane filtration arrangements.

A membrane filtration arrangement can be used in a submerged MBR system or a side-stream MBR system. In a side stream system, the membrane filtration arrangement would be placed outside the bioreactor while in the submerged system the membrane filtration arrangement would be placed in the bioreactor.

The outlet of a membrane filtration element can be further connected to an outlet tubing. The diameter of the tubing can be chosen to increase the permeate velocity to a minimum level to reach the detection level of a permeate velocity sensor located at the end of the outlet tubing. To increase permeate velocity, the inner diameter of the outlet tubing connected to the outlet of a membrane filtration element is smaller than the inner diameter of the outlet of the membrane filtration element. The outlet tubing can be provided as further element which is connected to the outlet of a membrane filtration element or forms an integral part of the cap further described below.

Figure 7:
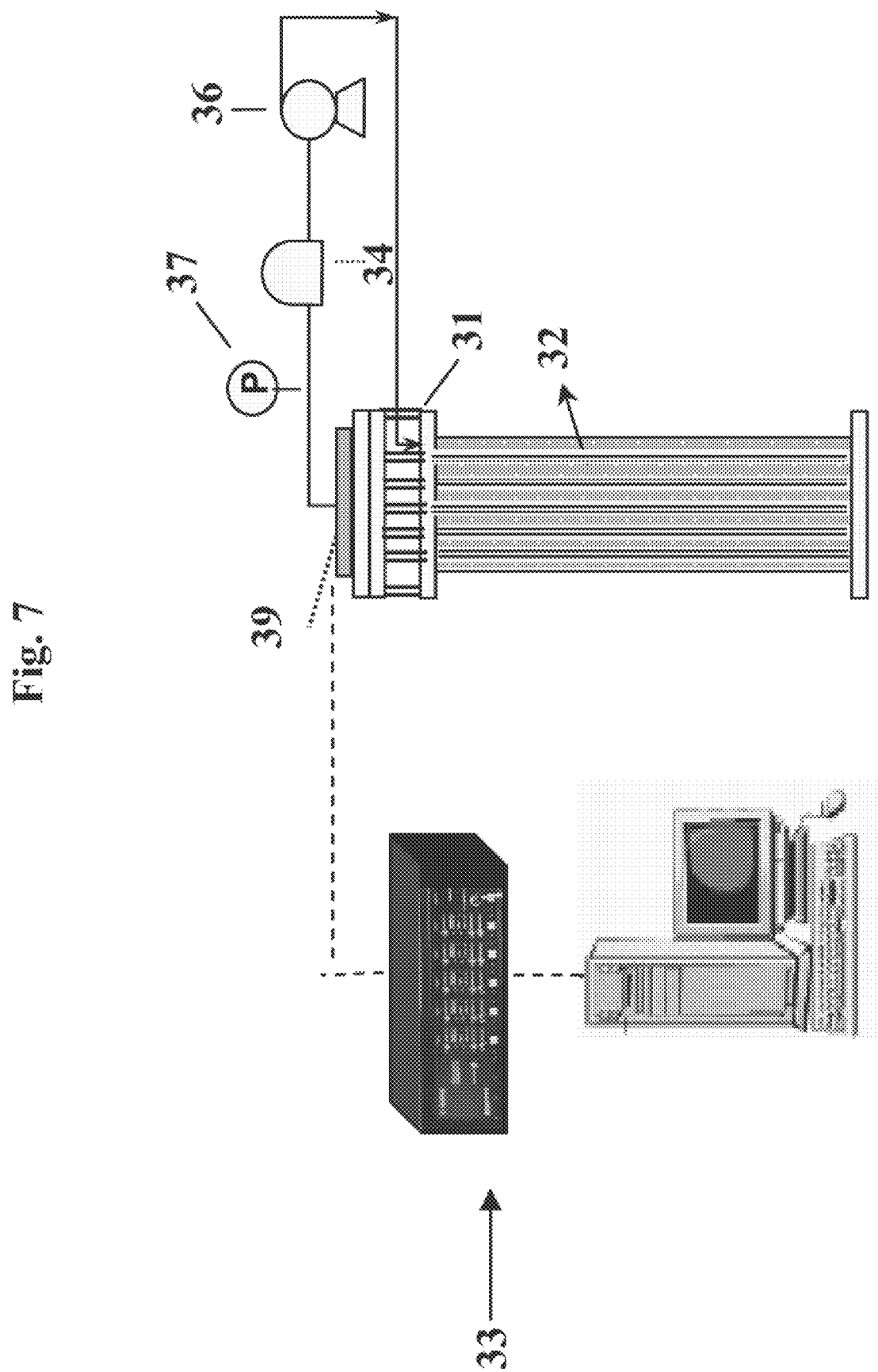
FIG. 7 shows a schematic overview of the experimental setup illustrated in FIG. 6A.

An exemplary embodiment using outlet tubings is shown in FIG. 7 in which the membrane filtration arrangement 32 comprises five different hollow fiber bundles. Permeate obtained in these fiber bundles is passed through the outlet tubings 31 (in FIG. 7 only four are shown) to the sensor matrix arranged in the cap 39. In this specific example, the vertical distance between the outlets and the sensors was 6 mm. However, the distance can vary depending on the permeate flow velocity and the detection range of the sensors of the sensor matrix.

A sensor used in the sensor matrix is arranged at the outlet to allow measuring of velocity of permeate exiting a membrane filtration element through its outlet, i.e., the position of the sensor is adapted to measure the velocity of permeate at the outlet of a membrane filtration element. In one embodiment, illustrated in FIGS. 1A and 1B, the sensor 10 is positioned at the opposed site of the outlet 20 of a membrane filtration element 30 which means that the sensor can be located on the opposed site but not directly opposite the outlet opening of the membrane filtration element. The sensor can be slightly offset as long as it is still possible to measure the velocity of the permeate exiting through the outlet of a membrane filtration element.

In another embodiment the sensor is located opposite an outlet, wherein opposite means the sensor is placed, or lying face to face with the outlet opening. In another embodiment it is also possible that the detecting surface of the sensor, i.e., the area of the sensor measuring the velocity, is positioned in an angle of between about 10, 20, 30, 40 or 50 to about 60, 70, 80 or 90° to the outlet of the membrane filtration element. In one example, illustrated in FIG. 1B, the sensors 10 are positioned on the opposed side of the outlets 20 at an angle of 30°. It can also be possible that the position of different sensors or groups of sensors in a sensor matrix with respect to the outlets differ from each other.

The sensor used is a sensor adapted to measure the velocity of the permeate stream exiting through the outlet of the membrane filtration element. Sensor types that can be used to measure the velocity of the permeate stream include, but are not limited to, thermal anemometer sensors, piezoelectric sensors and MEMS (Micro Electro Mechanical Systems) type flow sensors and the like. In general, any type of flow sensor can be used as long as it can be introduced in a sensor matrix in a non-invasive manner, i.e., it is not changing the flow of liquid, i.e., permeate, it is supposed to measure.

Hot wire anemometry (HWA) technique has been used for velocity measurement since the late 1800s. This technique relates heat transfer (from a heated wire to the surrounding) to the fluid velocity. Another version of HWA with lower contamination tendency and less susceptible to sensor damage is hot film anemometry (HFA). The operation of HWA or HFA in a constant temperature mode is known as constant temperature anemometry (CTA). This velocity measurement technique can be considered as relatively low cost, simple, and provides good frequency response.

The primary principle of constant temperature anemometry operation is based on the convective heat transfer from the heated element to the surrounding fluid. Any changes in fluid velocity will alter the convective heat transfer coefficient thereby affecting the sensor temperature. In order to maintain the temperature, the amount of electric current supplied to the sensor will also change to achieve a new equilibrium. The variation of the current supplied to the sensor can thus be associated to the changes in fluid velocity. Hot wire as well as hot film anemometry sensors can be used.

Figure 5:
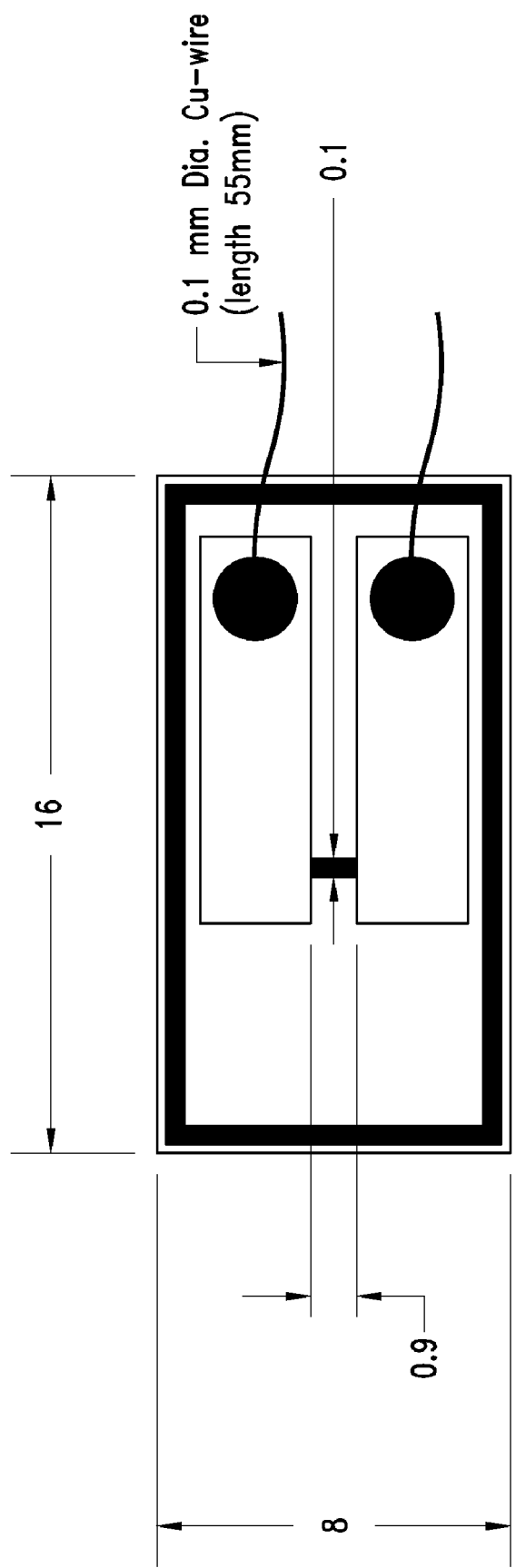
FIG. 5 shows an example of a constant temperature anemometry (CTA) sensor (glue-on probe, 55R47) manufactured by Dantec Dynamics which was used for flow distribution measurements described herein.

To avoid flow disturbances it might further be suitable to use flat sheet sensors, such as hot film anemometry sensors. Flow disturbances might occur when using sensors, such as a hot wire anemometry sensor, which uses a wire for measurement which can alter the flow of permeate whose velocity is to be measured by the sensor. Flat sheet sensors would not obstruct the permeate flow and thus can provide more accurate measurement results. An example of a flat sheet anemometry sensor is illustrated in FIG. 5 (see also experimental section).

A sensor comprises a detecting area. To protect the detecting area against abrasion caused by the constant flow of permeate the sensor can be coated with a thin protective layer. The layer thickness is adjusted to not decrease the sensitivity of the sensor. The material used for the protective layer can include, but is not limited to silicon dioxide, or commercial available lacquers, such as a lacquer also used for wood coating. In general, a lacquer is understood to be any of various clear or colored synthetic coatings made by dissolving nitrocellulose or other cellulose derivatives together with plasticizers and pigments in a mixture of volatile solvents.

The sensors can be connected via a wiring system to a computer system, such as the computer integrated StreamLine system 33 shown in FIG. 7 from which the sensors also receive their power. However, in large scale applications wiring might not be suitable and therefore RFID tags or other wireless connections can also be used to supply power to the sensors of the sensor matrix and to transfer data to a computer system.

The number of sensors used in a sensor matrix depends on the number of membrane filtration elements used in a membrane filtration arrangement. The number of sensors should equal the number of membrane filtration elements in the membrane filtration arrangement. However, it is also possible to run a system with a sensor matrix in which the number of sensors does not equal the number of outlets, i.e., the number of membrane filtration elements.

For example, in one embodiment the at least two membrane filtration elements are hollow fiber filtration membranes. Each of the hollow fiber filtration membranes comprises multiple hollow fibers each having an outlet for permeate. In this embodiment a sensor matrix can be used comprising at least two sensors. These at least two sensors are located above or on the opposed side of the multiple outlets of the hollow fibers of the hollow fiber filtration membrane.

The sensor matrix can be located in a cap which is affixed to the end of the membrane filtration arrangement comprising the outlets of the membrane filtration elements. Using a removable cap further allows taking off the cap from the membrane filtration arrangement, replacing a fouled element of the membrane filtration arrangement with a new membrane filtration element and reattach the cap to the membrane filtration arrangement.

Figure 4B:
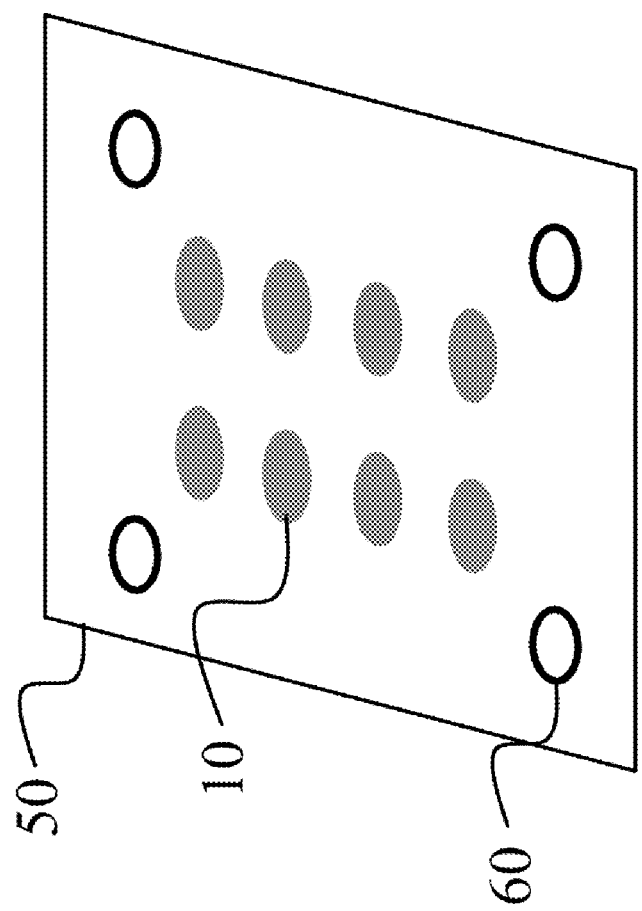
FIGS. 4A and 4B shows the top view of two different rectangular caps 50 with multiple sensors 10. The cap 50 in FIG. 4A comprises only one central outlet located between two sensors while the cap 50 in FIG. 4B comprises eight sensors 10 and four outlets 60 which are located in the upper and lower corners of the cap 50.
Figure 4A:
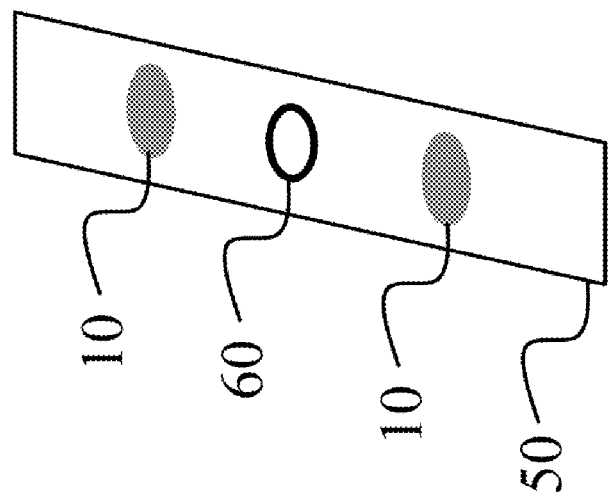

The shape of the cap is adapted to fit onto a membrane filtration arrangement. The cap further comprises at least one common outlet through which permeate from each of the at least two membrane filtration elements exits the cap. Examples, for such a common outlet or common outlets 60 are illustrated in FIGS. 3A, 3B, 4A and 4B. A common outlet 60 can be located in the center of the cap as illustrated in FIGS. 3A, 3B and 4A or it can be located at the sides or corners of the cap as for example illustrated in FIG. 4B. The arrangement of outlets in the cap also depends on the direction of the permeate flow within the cap. FIG. 9A illustrates an example of a round cap 50 comprising a central outlet for permeate surrounded in a circle by five sensors 10. The arrows in FIG. 9A indicate the direction of flow within the cap.

The sensor can either be embedded in the surface of the cap facing the outlets or is fixed on the surface of the cap facing the outlets. Sensors can be fixed to the surface of the cap by mechanical means or by gluing them on the cap surface. An example for a cap 50 comprising embedded sensors 10 is illustrated in FIG. 3B while FIG. 3A shows an example of a cap 50 with a fixed on or glued-on sensor 10.

Besides providing a flow distribution measuring system with a sensor matrix comprising only sensors for measuring the velocity of permeate flow it is further possible to add sensors to the sensor matrix measuring other parameters than the velocity of the permeate. Using sensors measuring the permeate conductivity which might for example be useful for reverse osmosis applications as the conductivity of permeate is influenced by its salt content.

In another aspect, it is referred to a cap as just described. The cap can comprise a sensor matrix comprising sensors adapted to measure the velocity of permeate exiting through outlets of a membrane filtration arrangement;

wherein the cap is adapted to be affixed on a membrane filtration arrangement; and wherein the cap comprises at least one outlet through which permeate exits the cap.

In another aspect, it is referred to a method adapted to measure the flow distribution in a membrane filtration arrangement comprising:

providing a flow distribution measuring system as described above; and measuring the individual permeate flow velocity at each outlet of the membrane filtration arrangement to determine the flow distribution pattern in the membrane filtration arrangement.

In a further aspect of the present invention a flow distribution measuring system is provided which comprises a sensor matrix adapted to measure the flow distribution of permeate passing through a hollow fiber filtration membrane;

wherein the hollow fiber filtration membrane comprises multiple hollow fibers each having an outlet for permeate;

wherein the sensor matrix comprises at least two sensors measuring permeate velocity; and wherein the at least two sensors are arranged above the multiple outlets of the multiple hollow fibers.

Other than in the embodiments described previously, in this embodiment a hollow fiber filtration membrane is used comprising a bundle of multiple hollow fibers. Each fiber has its own individual outlet. In this embodiment, the sensor is not located at a common outlet of such a fiber bundle as shown in FIG. 2B but a matrix of sensors is located directly above or on the opposed site of the multiple outlets of the hollow fibers of the hollow fiber filtration membrane. An example for such an embodiment is illustrated in FIG. 2C. In FIG. 2C the sensor matrix with the sensors 74 is located on the opposed side of the outlets of the hollow fibers 76 of the hollow fiber filtration membrane 70. Apart from that this embodiment shares the same features with the embodiments described further above.

The sensor matrix in this embodiment provides information about the condition of a group of hollow fibers in the bundle of hollow fibers which form part of the hollow fiber filtration membrane 70. Such a configuration provides even more precise information about the status of a hollow fiber filtration membrane as it allows determining the status of a group of hollow fibers within a hollow fiber filtration membrane rather than only about the whole hollow fiber filtration membrane as such.

For example, based on this configuration if a sensor indicates that a certain region of hollow fibers within the hollow fiber filtration membrane 70 has a higher tendency to be fouled compared to other regions, then the packing density can be modified, or the aeration can be changed by re-arranging the air or oxygen diffuser to deliver more intense air bubbles or more frequent aeration to the area that is more likely to be fouled. Depending on the setup of the hollow fiber filtration membrane, smaller sections of hollow fibers can be replaced by new hollow fibers.

In line with this embodiment, the present invention also refers to a cap comprising a sensor matrix which comprises sensors measuring the velocity of permeate exiting through multiple outlets of hollow fibers of a hollow fiber filtration membrane. The cap is adapted to be affixed on the hollow fiber filtration membrane; and the cap comprises an outlet through which the permeate exits the cap. Such a configuration is illustrated in FIG. 2C, which shows a cap 71 in which the sensors 74 are arranged. Each of the sensors measures the permeate flow velocity of a group of hollow fibers located in the immediate surrounding of the sensor 74. The cap has an outlet 73 through which permeate collected in the cap exits the cap.

Furthermore, the present invention refers to a method of measuring the flow distribution in a hollow fiber filtration membrane. This method includes providing a flow distribution measuring system as described above which uses a hollow fiber filtration membrane and measuring the permeate flow velocity above the outlets of the hollow fibers of the hollow fiber filtration membrane to determine the flow distribution pattern in the hollow fiber filtration membrane.

Another method refers to the measuring of the flow distribution in a hollow fiber filtration membrane wherein this method comprises providing a cap as described for a system which uses a hollow fiber filtration membrane;

affixing the cap to an end of the hollow fiber filtration membrane, wherein the end comprises the outlets of the multiple hollow fibers comprised in the hollow fiber filtration membrane; and measuring the permeate flow velocity above the outlets of the hollow fibers of the hollow fiber filtration membrane to determine the flow distribution pattern in the hollow fiber filtration membrane.

The system, cap and methods described herein can be used to reveal the progress of membrane fouling by detecting permeate velocity variations of individual membrane filtration elements or even within hollow fiber filtration elements during operation, i.e., filtration. The accuracy can be high and the discrepancy was less than 5% when comparing the flux values recorded with the sensor matrix referred to herein to those of manual measurements.

Use of flat sheet sensors, such as hot film anemometry sensors can further contribute to the improvement of the system due to their lower costs and smaller footprint. Such flat sheet sensors are less invasive as they do not require support. Due to the easy handling of such flat sheet sensors, more of them can be installed within the system. Since the sensors are located on the permeate side instead of the feed side of the system, a prolonged sensor lifetime can be achieved as frequent encounters with particles or contaminants present on the feed side and that can lead to sensor damage can be minimized.

The system, cap and methods described herein envisage that a sensor matrix located above membrane filtration elements can monitor local permeate flows and indicate local flux distributions. This system allows detection of fouling or blockage or mal-distribution or failure of aeration within one or multiple membrane filtration arrangement(s).

It has further been demonstrated that the information provided by a matrix of multiple permeate flow sensors proves to be much more informative than monitoring the changes in overall transmembrane pressure. Comparing the standard deviation of local permeate fluxes with the system, cap and method described herein with a locally fouled or blocked system provides a very sensitive tool for performance monitoring of one or multiple membrane filtration arrangements.

By "consisting of" is meant including, and limited to, whatever follows the phrase "consisting of". Thus, the phrase "consisting of" indicates that the listed elements are required or mandatory, and that no other elements may be present.

By "comprising" it is meant including, but not limited to, whatever follows the word "comprising". Thus, use of the term "comprising" indicates that the listed elements are required or mandatory, but that other elements are optional and may or may not be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Membrane Specification

The hollow fiber membranes used in the following experiments were manufactured by Singaport Cleanseas Pte. Ltd. The fibers were polyacrylonitrile (hydrophilic modified PAN) ultrafiltration membranes with 0.5 mm inner diameter and 1 mm outer diameter. Each fiber "bundle" had a diameter of 6 mm and consisted of ten hollow fiber membranes of 25 cm length (membrane area 0.00785 $m^2$) potted in a 1 cm length of hard tubing. When multiple fiber bundles were used in the experiments, they were carefully selected in an attempt to achieve an even permeability. The pure water permeability of the fibers was around 1.1 $L/m^2$ h*kpa±10%. The lower end of the fiber bundle was sealed with epoxy and permeate was withdrawn from the upper end. Following filtration, the hollow fiber membranes were washed using 1% of Terg-A-Zyme enzymatic detergent solution (Alconox, Inc.) for 15 minutes, rinsed with Milli Q water, followed by backwashing at 20 $L/m^2$*h for about three minutes. The measurement of water permeability after washing suggested that the membranes could be re-used as their permeability could be restored.

Sensor Specifications and Placement

Figure 6B:
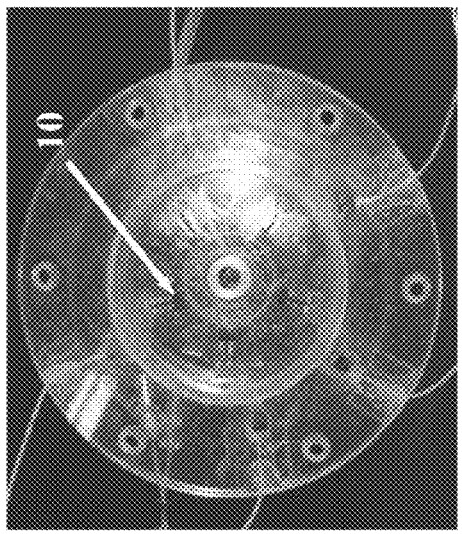
In FIG. 6B one of the five sensors 10 is indicated by an arrow. In the middle of the cap the outlet for permeate can be seen.
Figure 6C:
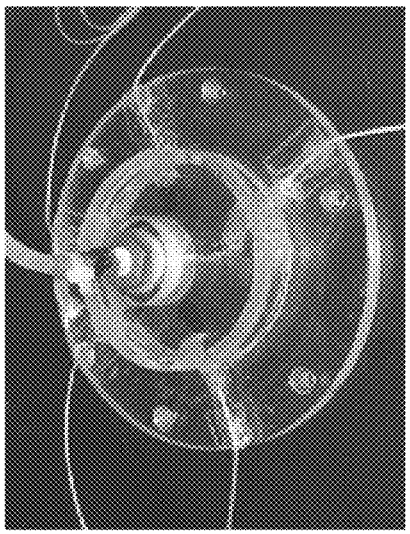
FIG. 6C shows a top view of the cap in which the tube connected to the outlet of the cap can be seen. The white cable which can be seen in FIGS. 6B and 6C indicate the connections of the sensors 10 to the StreamLine data logging system 33.
Figure 6A:
FIG. 6A shows the tank 32 with the cap fixed at the top end of the tank 32.

CTA sensors (glue-on probe, 55R47) manufactured by Dantec Dynamics were used for the flow distribution measurements (FIG. 5) and connected to a computer integrated StreamLine system. The use of glue-on probes offers an advantage over other types of probe due to their minimal space requirement and flow intrusion thereby reducing the flow disturbance. However, their sensitivities are generally low which poses a challenge in the typical low flow environment inside a membrane module. The glue-on probe was a nickel heating film (0.9 mm×0.1 mm) deposited on a polyimide foil (8 mm×16 mm×0.05 mm). A thin layer of silicon dioxide was deposited over the film as a protective coating. The sensor was connected to gold plated lead areas. As shown in FIG. 6B, a total of five glue-on probes 10 were fixed to the inner wall of the upper cap shown in FIGS. 6B and 6C of the Plexiglas tank 32 (10 cm diameter, 0.6 cm channel height) using epoxy (see also FIG. 6B and FIG. 9A). Each probe 10 was positioned above a fiber bundle outlet to enable measurement of individual permeate velocities. All sensors were oriented perpendicular to the direction of the flow. A thermocouple was connected to the StreamLine system 33 in order to monitor the ambient temperature changes.

Since the glue-on probes were designed for general applications in gases, modifications were performed to allow their applications in liquid by brushing the entire surface of the foil with a thin layer of lacquer to provide extra protection to the sensor. Lacquer was selected due to this substance being commonly used to repair minor fractures in the insulation coating of a hot film probe. It was important to control the thickness of the lacquer coating to achieve a uniform thickness so as not to reduce the sensitivity and frequency response while providing an adequate protection.

Another CTA consideration is the overheat ratio defined as follows:

$$\text{Overheat ratio} = R_w/R_a \quad (1)$$

$R_w$ is the resistance of the heated wire at temperature, $T_w$, while $R_a$ is the resistance of the wire at the ambient temperature, $T_a$. In order to achieve high velocity sensitivity, a high sensor temperature is desirable. However, an excessively high temperature should be avoided to prevent bubble formation and oxidation that may result in the reduction of probe life due to wire or film burnt out. Therefore, it is necessary to maintain an acceptable overheat ratio.

The selection of overheat ratio also depends on the sensor material. For applications in liquid, it is recommended to employ a low overheat ratio (around 0.1 for film probes) to prolong the sensor life. Therefore, a constant overheat ratio of 0.1 was maintained for all measurements in the present experiments. Frequent calibration of the probe has been reported as one alternative approach to maintain an acceptable probe response at a low overheat ratio.

Measurement Principal

Figure 26:
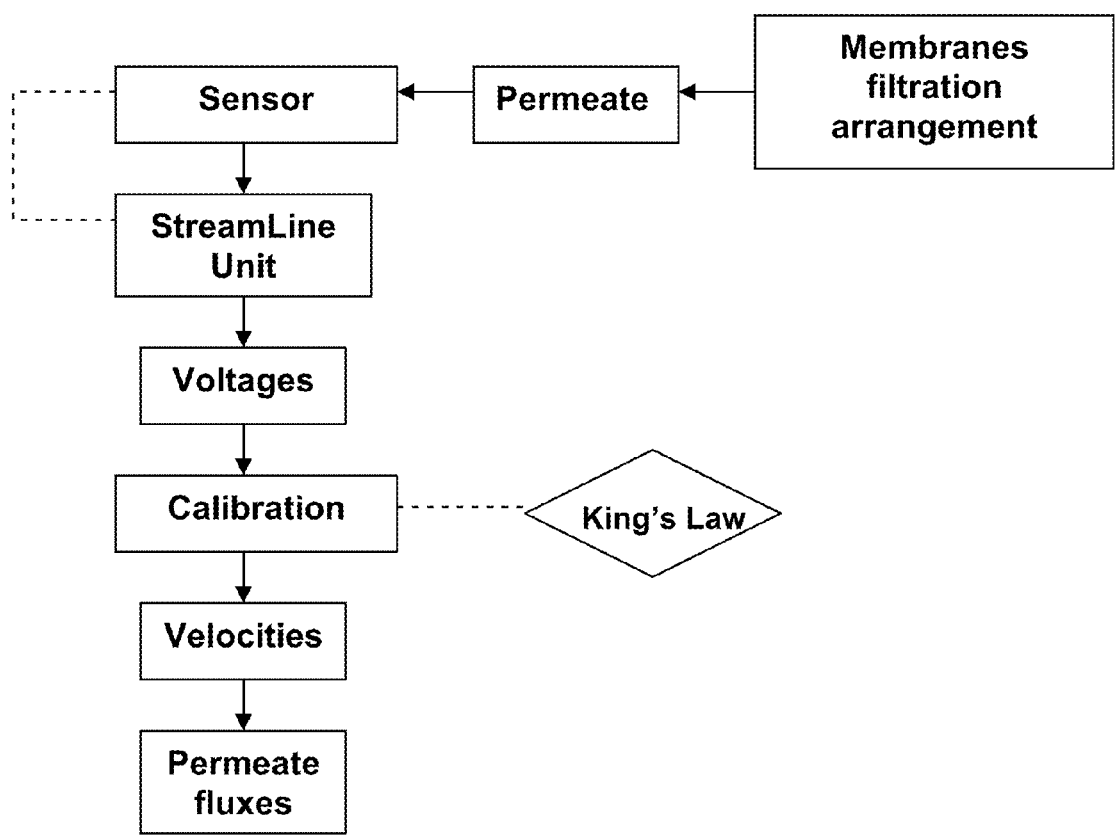
FIG. 26 illustrates the flowchart of measurement principles for the experiments referred to herein.

The flowchart of measurement principles for the experiments referred to in the following sections is given in FIG. 26. The velocity of permeate emerged from individual membrane bundles outlet is detected by commercially available hot film anemometry sensors (glue-on probe, 55R47 by Dantec Dynamics). The sensors are connected to a computer integrated StreamLine unit (Dantec Dynamics) that supplies power to the sensors and functions as a controller as well as data acquisitions. The sensors are pre-calibrated in-situ by relating the recorded signals to the known water velocities. The recorded signals are shown as output voltages and are converted to velocities by using a calibration curve. By knowing the cross sectional area of the permeate outlet and the membrane area, the individual flux and flux distribution of permeate can then be calculated.

Experimental Setup

The experimental setup is illustrated in FIG. 7. The five fiber bundles were mounted vertically onto a membrane holder 31 comprising two circular plates supported by two acrylic rods. The membrane holder 31 was immersed in a circular tank 32 made of acrylic with an inner diameter of 10 cm and a working volume of about 4 l. In order to enable the identification of fiber bundles, the bundles were numbered according to the configuration as presented in FIG. 8. The model particles used in membrane filtration runs were bentonite suspension in MilliQ water at definite feed concentration. The volume median diameter ($d_{50}$) of bentonite particles measured with Malvern Sizer hydro 2000SM was 3.2 μm. Prior to filtration, an in situ sensor calibration was performed by acquiring the CTA readings using deionized water at various flowrates. Further details of the calibration protocol are discussed further below.

The bentonite filtration experiments were conducted at a constant permeation flux for one to three hours. The variation of transmembrane pressure during the filtration was monitored by a pressure gauge (Cecomp Electronics Inc., USA, pressure range −101.33 to +101.33 kPa). The permeate was extracted using a Masterflex peristaltic pump 36, causing the permeate from each bundle to emerge from the permeate fittings, filling the upper cap 39, passing the CTA sensors to the main outlet, and then re-circulated to the Plexiglas tank to maintain a constant feed concentration and suspension level in the tank. The individual permeate velocities from each fiber bundle were simultaneously detected by the CTA probes connected to a computer. Since the permeate velocity (around $10^{-6}$ m/s) was much lower than the minimum detection limit of the sensor ($10^{-2}$ m/s), a piece of Masterflex microbore tubing (0.89 mm ID) was inserted and glued inside the permeate fitting (see FIG. 9) to increase the outlet velocity as a further modification to facilitate the CTA detection. Further development would be needed in both the CTA design and the cap surface geometry to extend the lower detection limit of the glue-on probes and CTA approach to a prototype setting.

Sensor Calibration

For liquid applications, the calibration of CTA sensors can be performed either by immersing a stagnant probe in a flowing fluid or traversing the probe at a defined velocity along a stationary fluid channel. The calibration can also be conducted by positioning a stationary probe in the discharge hole of a liquid filled container, although difficulties might arise when the liquid in the tank reaches a minimum level. Another option is in situ calibration. This technique is more appropriate for glue-on probes since the probes cannot be removed once they have been glued. A further advantage of the in situ option is that the conditions throughout the calibration and experiments will be similar.

In the present experiments, the procedures for the in situ calibration were performed as follows. Filtrations were carried out at various permeate fluxes using Milli-Q water. The total permeate flow rate was measured volumetrically, i.e., noting the time required to collect a certain volume of permeate. Since the permeabilities of five membrane bundles were identical, the individual permeate flow rate could be estimated as one-fifth of the total permeate flow rate. The calibrations of five sensors were conducted both simultaneously and independently. It was found that the results using both methods were similar. The output voltage at each permeate velocity was also recorded using the glue-on probes (five sensors for five fiber bundles). The CTA signals were obtained at various velocities up to about 0.1 m/sec. Each measurement was carried out for 10 seconds with a recording frequency of 100 measurements per second. The measurements were replicated to ensure the reproducibility of results. The recorded data at each velocity were averaged and the CTA signals were then plotted versus velocity.

Figure 10:
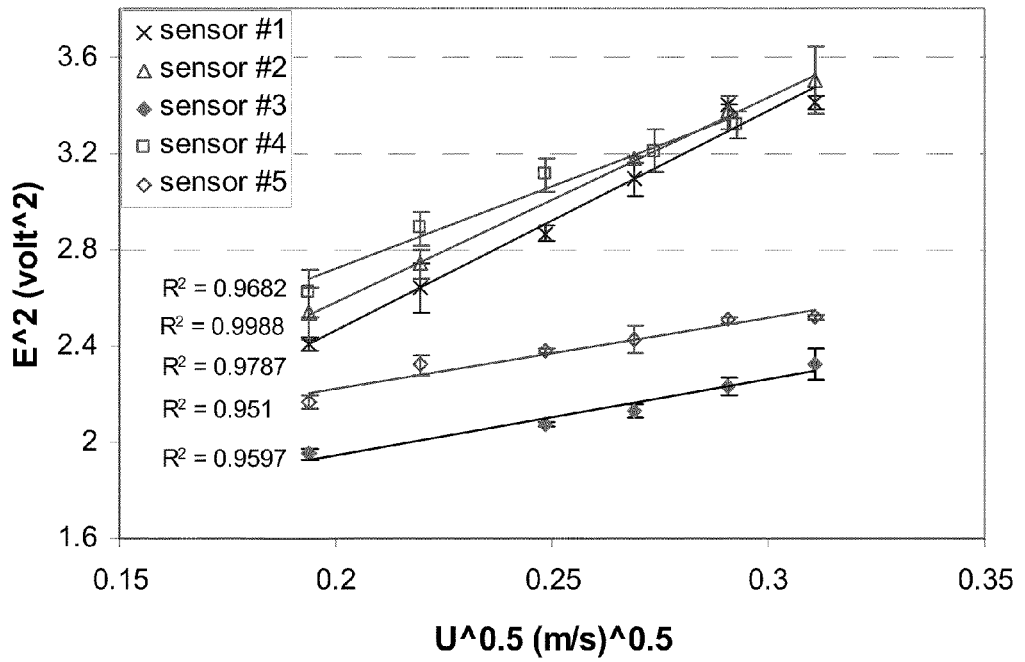
FIG. 10 indicates the results of the in situ calibration of the sensors used in the experimental setup illustrated in FIG. 6.

The relationship between CTA output voltages and velocities can be expressed using the heat transfer concept (King's law):

$$E_b^2 = A + B\,U^n \qquad (2)$$

Where $E_b$ is the anemometer output voltage, U is the fluid velocity, A and B are constants. The magnitude of the exponent, n, is velocity dependent and was reported to vary from 0.4 to 0.5. However, the above equation was suggested to be applicable at only moderate to high velocities. This is because at low velocities, the effect of free convection will become too pronounced. Despite this concern, the King's law provided acceptable results within the low recorded velocity range in the study, with n=0.5 and $R^2>0.95$ for all sensors (FIG. 10). The deviations of A and B constants for the five sensors tested were due to variations in sensor manufacturing; causing an individual sensor to indicate different response to the changes in liquid velocity. It can be seen that the A values vary by about 150% and B values by about 200%.

In terms of the temperature effect, it has been mentioned above that a constant overheat ratio was maintained throughout the experiments. Furthermore, the monitoring of ambient temperature variations during the experiments revealed that the fluctuations were negligible. Thus, there was no impact of ambient temperature drift on the experimental results.

Assessment of Sensor Sensitivity

Local Permeate Flow Measurement in a Submerged Membrane Filtration Arrangement with Multiple Membrane Filtration Elements (Fiber Bundles)

A submerged membrane filtration arrangement typically comprises multiple fiber "bundles" (membrane filtration elements) operating in parallel and connected to a common header. It is thus of interest to investigate if the CTA sensors can be used to detect localized fouling or blocking across the different bundles in our "model" system. Localized fouling could be caused by mal-distribution of flow due to poor hydrodynamic conditions. In the experiments described herein, a combination of "pre-fouled" and clean fiber bundles, as well as aerated and non-aerated membrane bundles, were used to simulate the localized fouling or blocking. Further details are discussed in the following sections.

Figure 11:
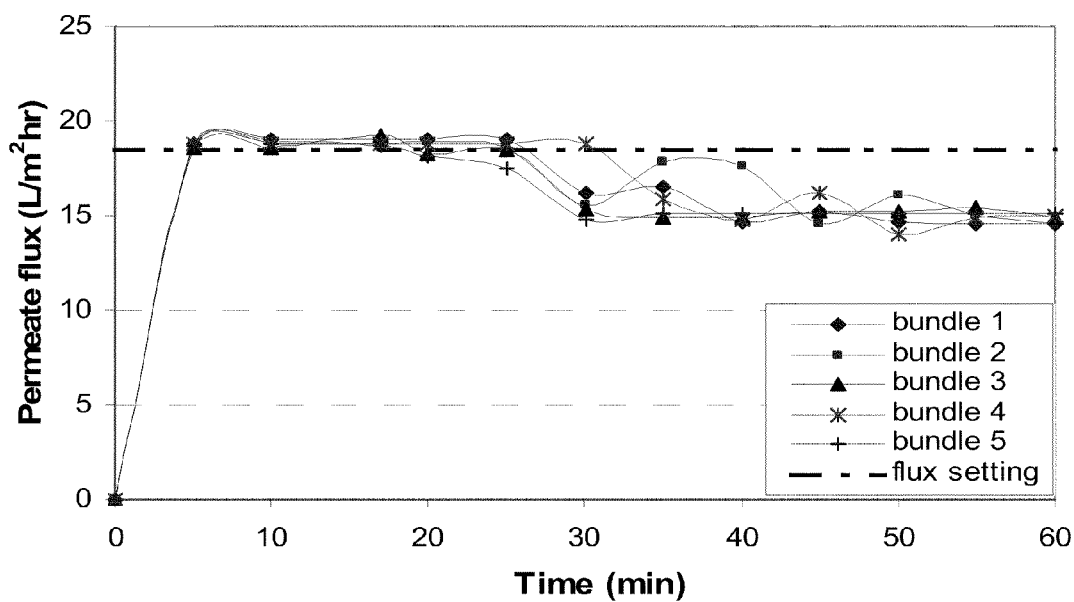
FIG. 11 shows the permeate fluxes recorded with the sensors used in the experimental setup illustrated in FIG. 6 during filtration of 2 g/L bentonite at initial 19 L/m$^2$ h operating flux (all bundles were clean at the onset of filtration).

System Containing all Clean Bundles at the Onset of Filtration in a Non-Aerated System When equally clean bundles were used at the onset of filtration, the permeate flux profile of each bundles measured by the CTA were found to be similar (FIG. 11). This could be due to the axisymmetric arrangement of the fiber bundles in the tank, thus each bundle had an identical fouling propensity. It required approximately 5 minutes for permeate to entirely fill the cap, thus it was not possible to conduct CTA reading prior to 5 minutes of filtration. FIG. 11 reveals that the system could maintain a constant flux operation until about 20-25 minutes of filtration. After that, the flux gradually decreased with an approximately 20% decrease in permeate fluxes after 60 minutes of filtration. This experiment was dead-end, without aeration and once the fouling progressed to a critical level, the suction pump could not cope, and then the flux would drastically decline. The manual measurements of the average permeate flow confirmed the decline in fluxes. By comparing the permeate fluxes recorded by CTA to the manual measurements, it was found that data obtained from both methods were very close with an average discrepancy of 2%.

After the filtration step, the cake layer on each fiber bundle was collected by backwashing for about three minutes to ensure that all the cake had been dislodged from the membranes. The deposit was then separated from the washing liquid by means of centrifugation at 4000 rpm for 10 minutes. The supernatant was discarded and the cake was dried in the oven at 105° C. overnight.

Figure 12:
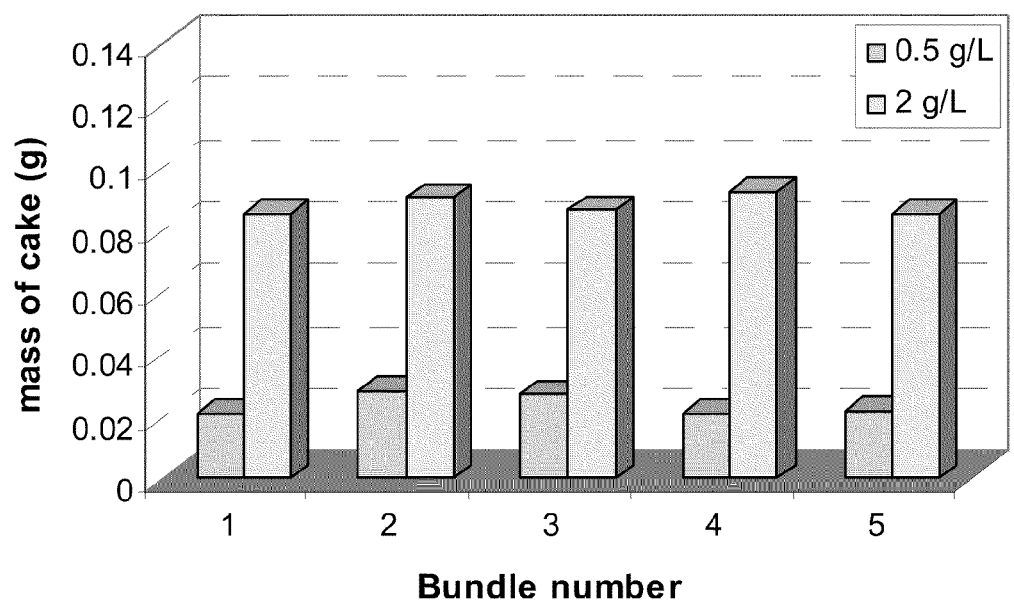
FIG. 12 illustrates the mass of cake deposited on each hollow fiber bundle after one hour of filtration at 19 L/m$^2$ h (0.5 and 2 g/l bentonite) with all bundles being clean at the beginning of filtration.
Figure 13:
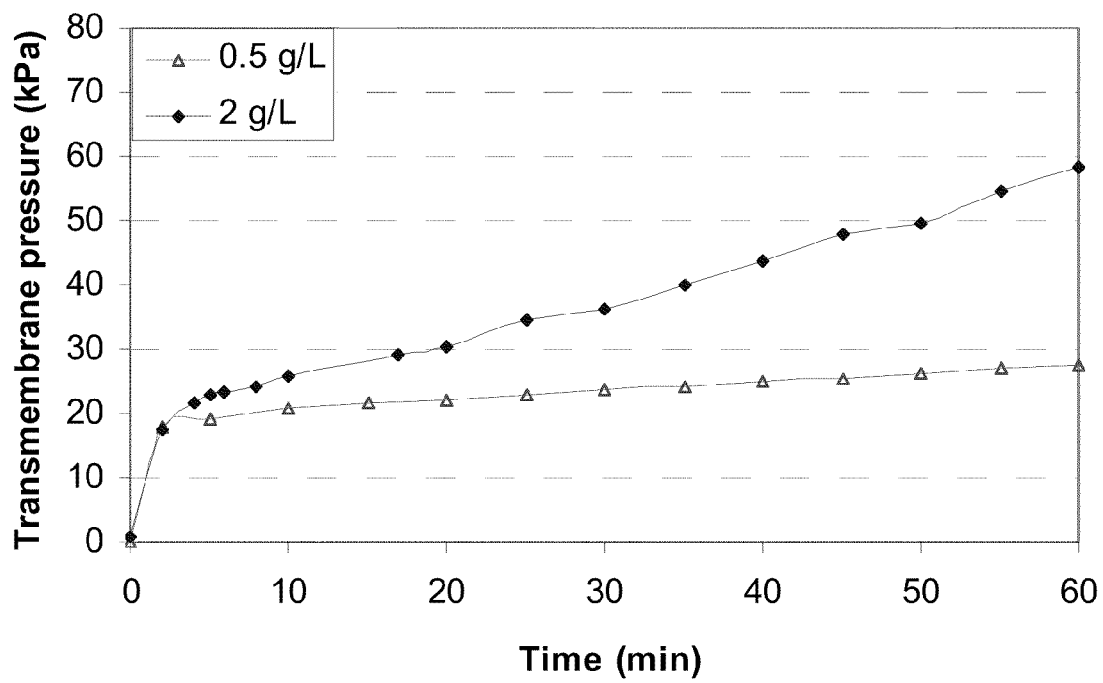
FIG. 13 illustrates the variations of transmembrane pressure during filtration of 0.5 and 2 g/L bentonite at 19 L/m$^2$ h which permeate fluxes and mass of cake are shown in FIGS. 11 and 12.

All the fiber bundles were equally susceptible to fouling as shown by the similar masses of dried cake on each bundle after filtration (FIG. 12). This even fouling distribution agreed with the CTA readings. The results also demonstrated that four times increase in feed concentration (from 0.5 g/L to 2 g/L bentonite) caused approximately four times increase in both the mass of cake (0.02 g to 0.08 g) (FIG. 12) and the fouling rate or d(TMP)/dt values (0.167 kPa/min to 0.683 kPa/min) (FIG. 13).

Mal-distribution of Flow with "Used" and Clean Bundles in a Non-Aerated System One option to create mal-distribution of flow in the system was by using membrane bundles with different states of fouling. One bundle (bundle #3) was intentionally "pre-fouled" by performing the filtration 2 hours ahead of the other bundles in a 2 g/L of bentonite suspension at a predetermined feed pumping speed that was equivalent to an initial flux of approximately 19 L/m$^2$*h, while the other fiber bundle outlets were blocked. Afterwards, the filtration was carried on using the "used" bundle together with the four clean bundles.

Figure 14:
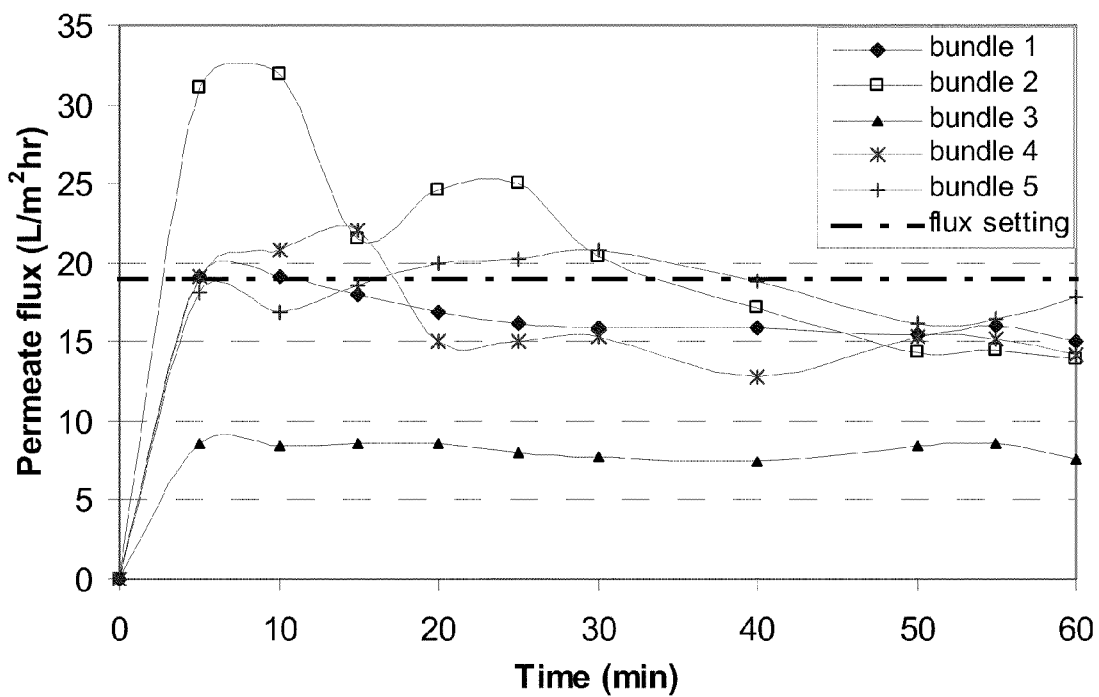
FIG. 14 illustrates the variation of permeate fluxes recorded with the sensors used in the experimental setup illustrated in FIG. 6 during filtration of 2 g/L bentonite at 19 L/m$^2$ h wherein bundle 3 (black triangle) had been "pre-fouled".

FIG. 14 illustrates the permeate flux variations of individual fiber bundles recorded by the CTA. Since bundle #3 had been formerly used, its permeate flux remained low (around 7.5 to 8.5 L/m$^2$ hr) throughout the filtration. The poor performance of bundle #3 caused the permeate load to be distributed among other bundles although it was not evenly distributed. There was a substantial increase in the permeate flux of bundle #2, rising up to more than 30 L/m$^2$*h when filtration was initiated. Thereafter the bundle #2 flux steadily declined to about 14.5 L/m$^2$*h by the end of the experiment and was then marginally lower than the other initially clean bundles (#1, 4 and 5). Bundles #1, 4 and 5 exhibited similar trends to bundle #2 but only showed minor initial flux rises compared with #2; bundle #4 showed a somewhat higher peak (22 L/m$^2$*h) than bundles #1 and 5. The average discrepancy between CTA readings and manual measurements was relatively low at 4.7%.

Figure 15:
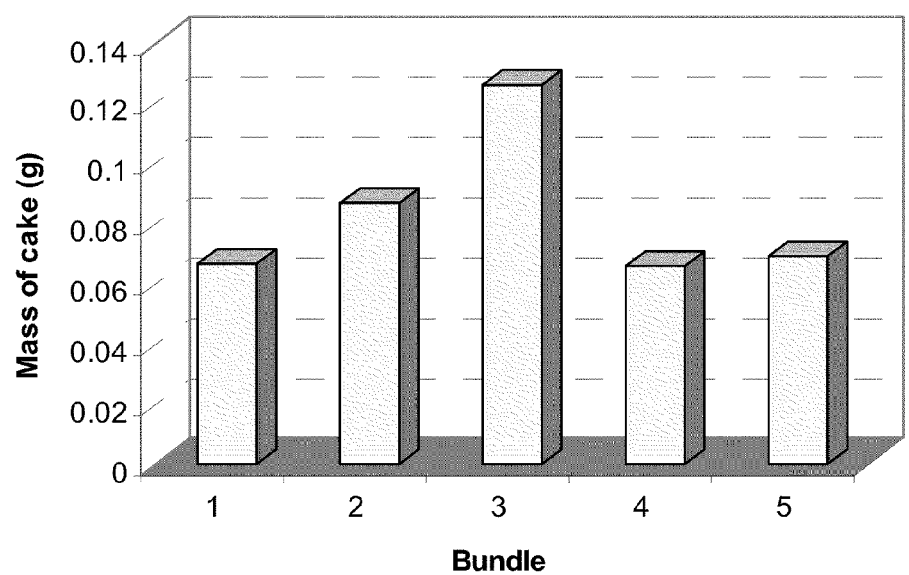
FIG. 15 illustrates the mass of dried cake collected from each hollow fiber bundle after 60 minutes of filtration of 2 g/L bentonite (operating flux 19 L/m$^2$ h) with bundle #3 being "pre-fouled".

When comparing the mass of cake deposited on each fiber bundle after 60 minutes of filtration as depicted in FIG. 15, it is apparent that bundle #3 has the largest amount of cake with the second largest on bundle #2. The remaining bundles had nearly identical amounts of cake. These outcomes reflected the CTA readings in the same manner: the worst performance of bundle #3 has the greatest amount of cake. A sudden rise of permeate flux of bundle #2 would have caused the convection of more particles towards the membrane surface and over the period of the experiment, bundle #2 filtered approximately 30% more than bundles #1, 4 and 5. This compares with the cake loadings of about 0.08 and 0.06, respectively. Consequently, significant flux decline occurred for bundle #2 due to fouling. Almost identical amounts of cake on bundles #1, #4 and #5 indicate similar performance of the respective bundles as shown in FIG. 14.

Figure 16:
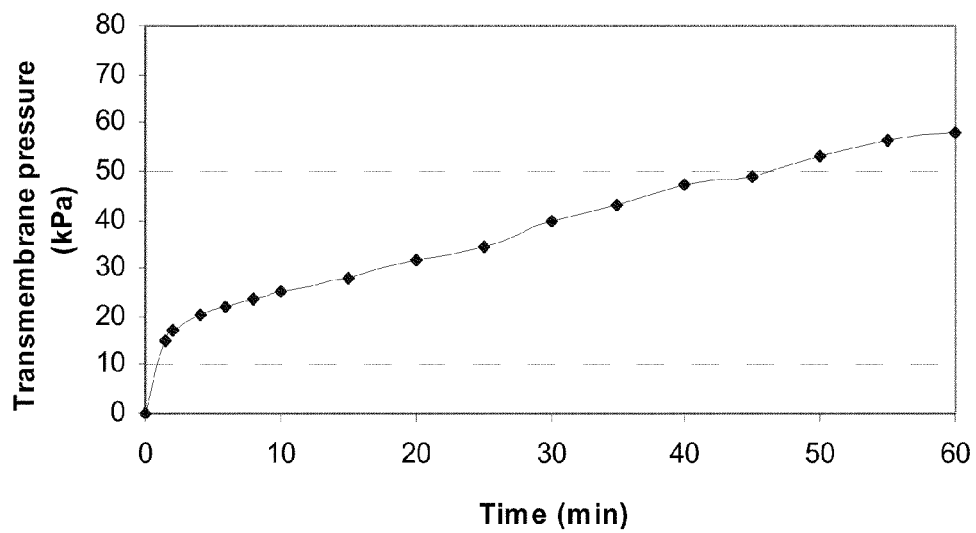
FIG. 16 illustrates the profile of transmembrane pressure during filtration of 2 g/L bentonite with bundle #3 being "pre-fouled".

Despite the mal-distribution of flux and fouling, the transmembrane pressure values (FIG. 16) were similar to those with an evenly distributed flow (FIG. 13). This is important as it shows that overall TMP history is not a sensitive indicator of the complex variations in flux and fouling distribution that were occurring simultaneously. These observations strengthen the argument for better local monitoring of system performance.

Permeate Flow Measurement During Filtration in an Evenly Aerate System

Figure 17:
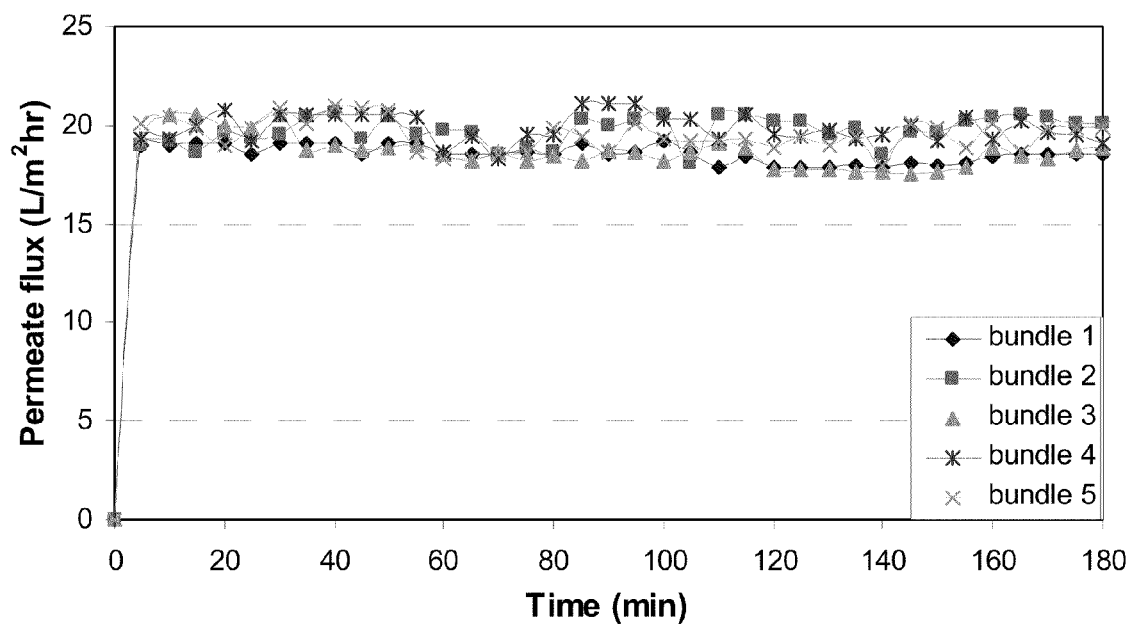
FIG. 17 illustrates permeate flux profiles during filtration with all aerated bundles (2 g/L bentonite, operating flux 19 L/m$^2$ h, 2 L/min air flowrate).
Figure 19:
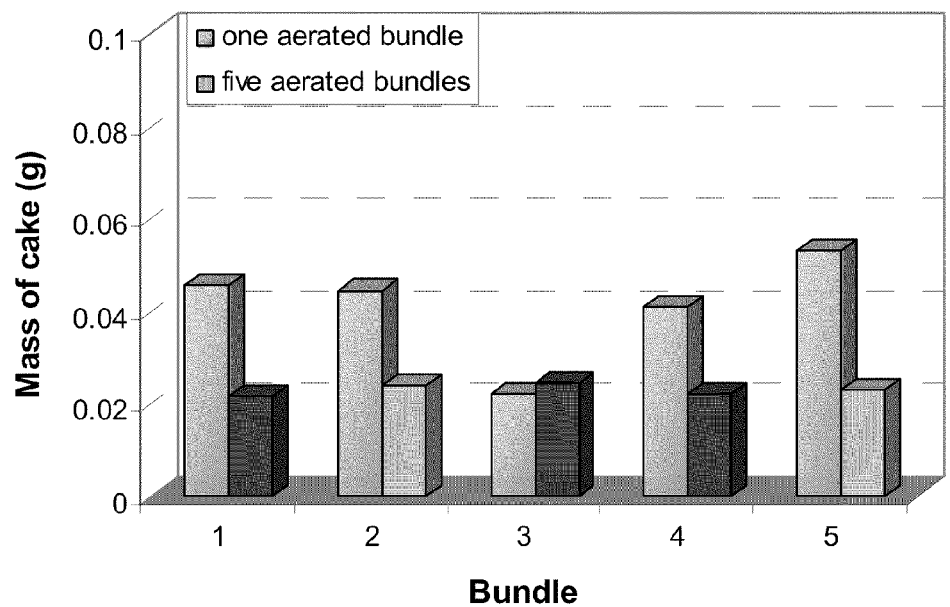
FIG. 19 illustrates a comparison of bentonite cake deposited on each hollow fiber bundle after three hours of filtration with one aerated bundle (bundle #3) and five aerated bundles (19 L/m$^2$ h, 2 g/L bentonite).
Figure 20:
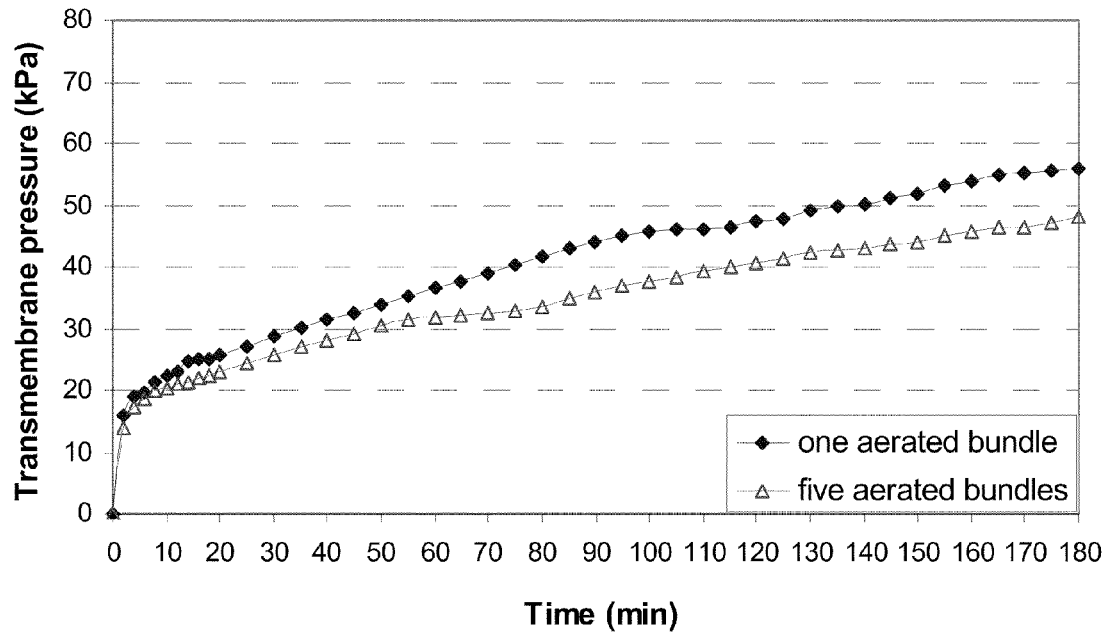
FIG. 20 illustrates a comparison of transmembrane pressure values of systems under various conditions: with one aerated hollow fiber bundle and with all hollow fiber bundles aerated (19 L/m$^2$ h, 2 g/L bentonite).

FIG. 17 illustrates the permeate fluxes of a system with all bundles aerated recorded by CTA sensors, while the amounts of cake deposited on each fiber bundles and the transmembrane pressure values are plotted in FIG. 19 and FIG. 20, respectively. The filtration was operated at 19 L/m$^2$*h and air bubbles were introduced at 2 L/min below each membrane bundle. As expected, constant flux conditions could be maintained throughout the filtration duration and differential fluxes among bundles were insignificant. An even flow distribution among aerated bundles was also confirmed by comparing the amounts of cake accumulated on individual membrane bundles (FIG. 19). For this study, the disparity between average flux recorded by the sensors and the operating flux was 2.2%.

Mal-Distribution of Flow Due to Uneven Aeration

Figure 18:
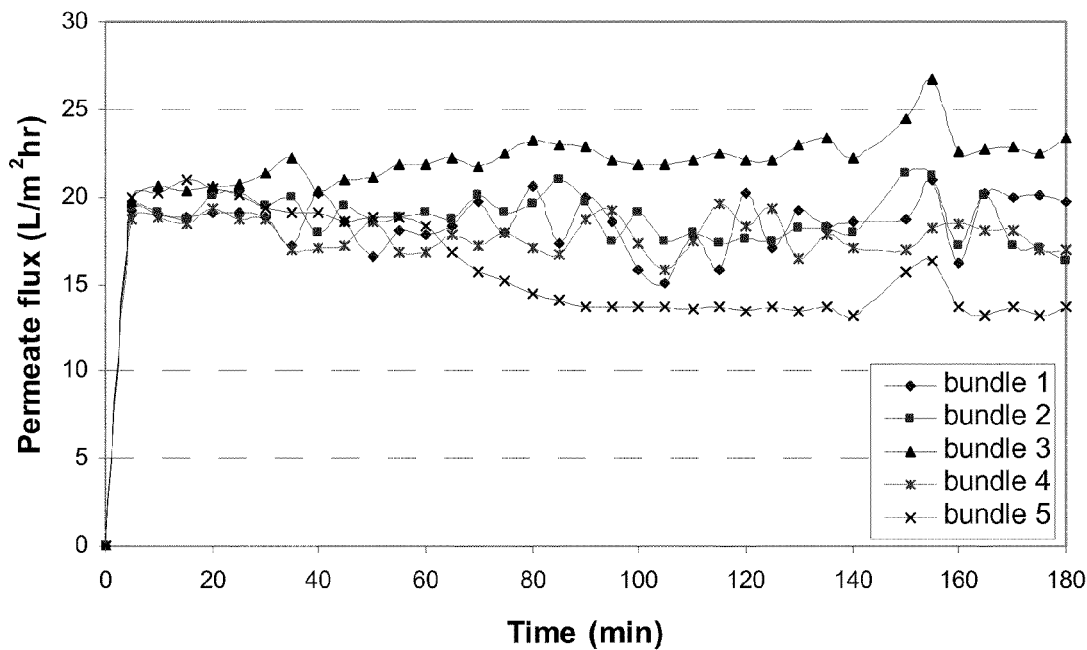
FIG. 18 illustrates permeate flux profiles of a mal-distributed system containing one aerated and four non-aerated membrane filtration elements (hollow fiber bundles) during filtration of 2 g/L bentonite (air bubbles were introduced at bundle #3 (black triangle) at 2 L/min).

FIG. 18 shows the variation of permeate fluxes in a mal-distributed system comprising one aerated bundle (bundle 3) and four non-aerated bundles obtained from CTA readings. Air bubbles were introduced below bundle 3 through a 1 mm single nozzle at 2 L/min aeration rate. The readings revealed that the permeate fluxes of all fiber bundles were relatively uniform (approximately 18.4 to 20 L/m$^2$*h) for the first 30 minutes, after which they started to deviate with the permeate flux of the aerated bundle rising to about 12 to 30% greater than its counterparts, showing that the air sparging could reduce the cake deposition on the membrane surface. Despite the filtration being operated at a constant flux, the fluxes of the non-aerated bundles declined gradually to about 13.5-17 L/m$^2$*h after three hours of operation due to fouling. It appeared that the "cleaner" aerated bundle (bundle #3) had partially compensated for the loss of performance of the non-aerated bundles. The average fluxes obtained by CTA readings were close to the operating flux with an average discrepancy of 3.5%.

The amount of bentonite cake deposited on each fiber bundle during this experiment is presented in FIG. 19. The cake distribution results reflect identical trends to the permeate flux profiles: the aerated bundle obtained about 50% less deposit compared to other bundles, while the quantities of cake deposited on bundles #1, #2 and #4 were similar suggesting that their fouling rates were comparable. The highest amount of cake on bundle #5 reflects its greatest flux decline.

Compared with the study for five aerated bundles, the transmembrane pressure profiles were initially overlapped. However, after 30 minutes of filtration, the TMP values of the one aerated bundle experiment began to increase with a maximum of 25% higher than that for all aerated bundles (FIG. 20). As would be expected, a system with irregular aeration had a higher fouling propensity than an evenly aerated system. Again, the subtle effects of flux and fouling load distribution can not be deduced from the TMP history.

Transient Malfunction of Local Aeration

Since the CTA sensors have demonstrated their capabilities to respond to the variations of local permeate flow, it was further investigated how permeate would redistribute among the bundles when a mal-distribution of flow occurs instantaneously during a normal filtration. To simulate this, a filtration experiment with 2 g/L bentonite suspension was performed at 19 L/m² h constant flux for 60 minutes with all bundles aerated at 2 L/min. Between 60 to 120 minutes, the aeration of bundles #2 and #3 was temporarily switched off. After 120 minutes, the aeration of the respective bundles was resumed.

Figure 21:
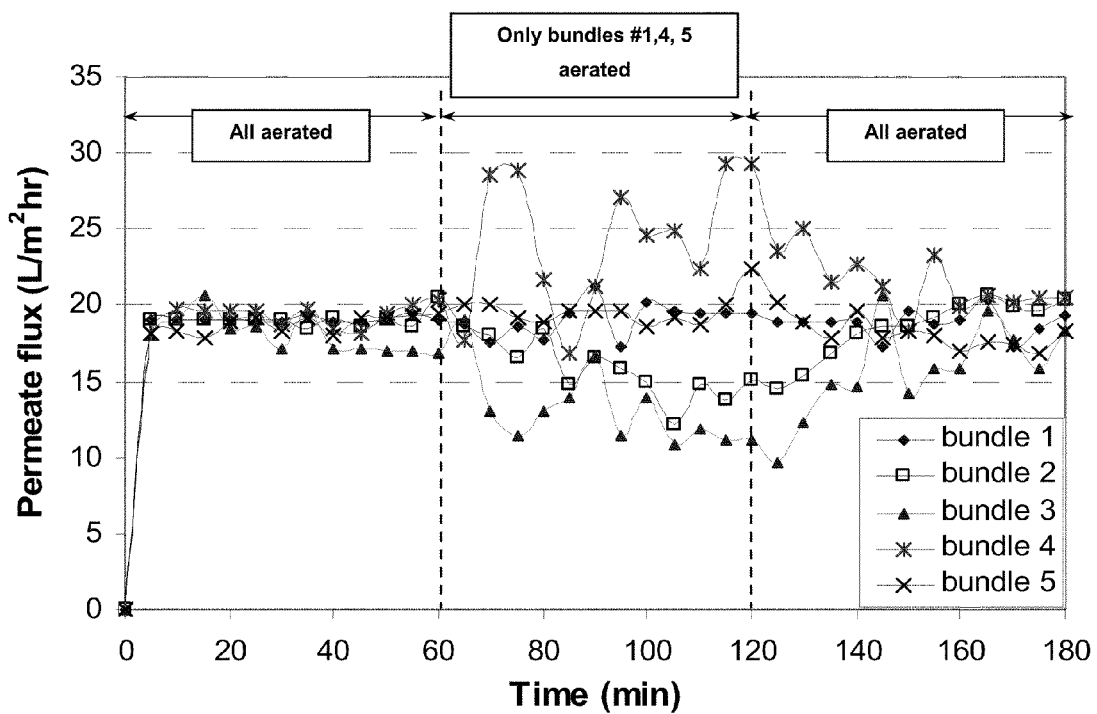
FIG. 21 illustrates the flux distribution during filtration of 2 g/L bentonite when transient malfunction of local aeration occurred between 60 to 120 minutes (aeration at bundles #2 (square) and #3 (black triangle) was temporarily unavailable).
Figure 22:
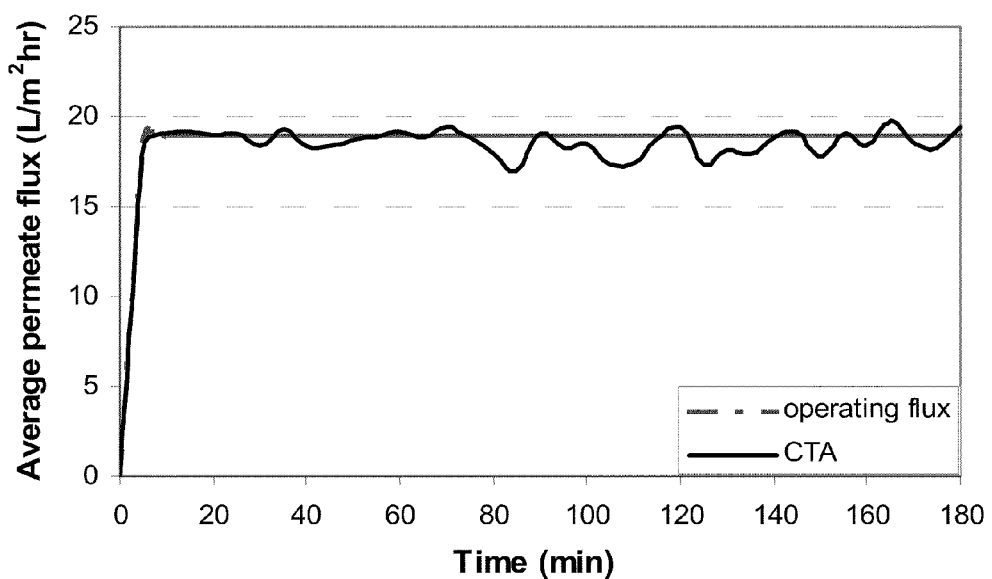
FIG. 22 illustrates a comparison of average permeate flux recorded by sensors used in the experimental setup illustrated in FIG. 6 to the operating flux (19 L/m² h).

The distribution of permeate fluxes recorded by the CTA sensors is illustrated in FIG. 21. Permeate was evenly distributed among five bundles during an initial stage when the supply of air bubbles was normal. Following a simulated aeration failure, erratic profiles of permeate flux occurred with substantial drops in permeate fluxes of the non-aerated bundles (bundles #2 and #3) and upsurge in fluxes of the aerated bundles that compensated for the imbalance of permeate flow. However, the extra permeate load was not evenly distributed, possibly due to changes in "permeate competition" and local aeration effects. When the air supply was returned to normal after 120 minutes of operation, it appeared that the system attempted to gradually balance out the permeate flow, indicating that air bubbles could scour the cake layer on the non-aerated bundles' surface. This ability to restore performance is encouraging but would be expected to depend on duration of aeration failure and nature of fouling (bentonite would be more reversible than biofloc). Despite the imbalance of fluxes due to the aeration malfunction, the average permeate flux remained close to the operating flux with only 3% discrepancy (FIG. 22).

Figure 23:
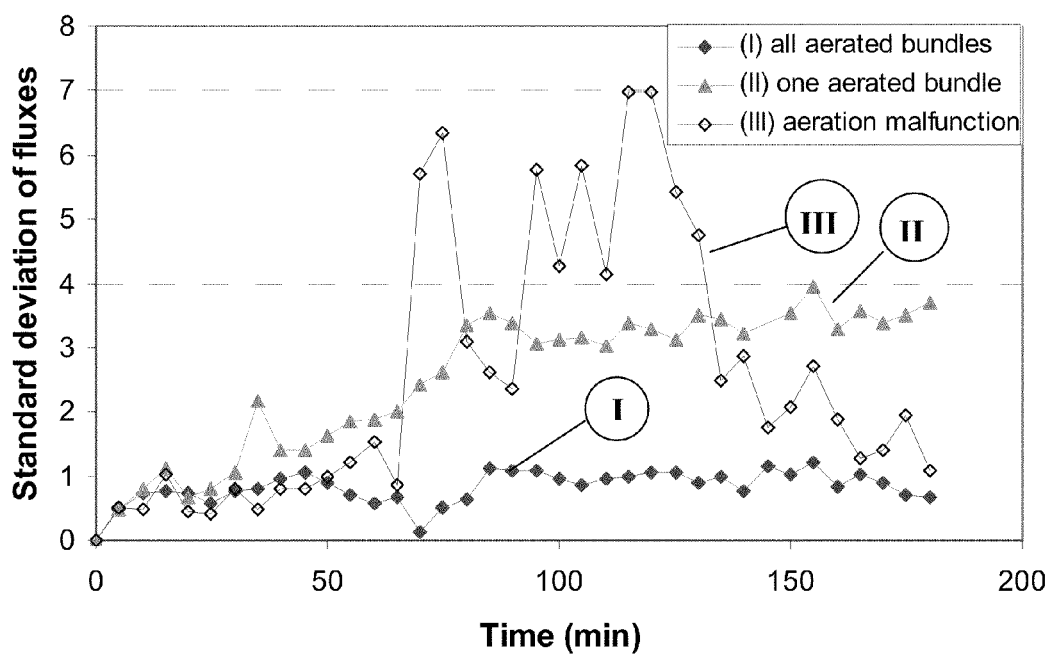
FIG. 23 illustrates the variation of standard deviation of fluxes of various systems during filtration. In a first system (I) all hollow fiber bundles were aerated; in a second system (II) only one hollow fiber bundle was aerated; in the third system (III) momentary local aeration malfunction occurred.

It is known that the standard deviation of fluxes is a sensitive indicator of performance loss. FIG. 23 compares the standard deviation of (bundle) fluxes of the various systems tested here. It is evident that the evenly aerated system had the lowest and most stable standard deviation (data I) with an average of 0.8. With only one aerated bundle, the standard deviation (II) gradually increased from an initial value of 0.8 up to 3.7 at the end of the filtration run, showing that the flux distribution was significantly uneven. For the system with the temporary malfunction of air supply, the standard deviation values (III) were identical to those with normal aeration during the first 60 minutes. A rapid increase in standard deviation occurred 10 minutes after termination of local aeration. When the local air bubbling was recommenced, the standard deviation then gradually declined approaching its initial values. This means that local monitoring of permeate flow by sensors, such as CTA, could potentially provide an early warning of fouling or blockage.

The cake mass data (FIG. 24) clearly match the permeate flow distribution results. Due to temporary cessation of air sparging for bundles #2 and #3, the cake quantities on these bundles surpass those of aerated bundles by approximately 26% and 50% more than the average quantity of the aerated bundles, respectively. The lowest flux bundle #3 results in the greatest amount of cake. Evidently, the cake quantity correlates with the magnitude of fouling.

Figure 25:
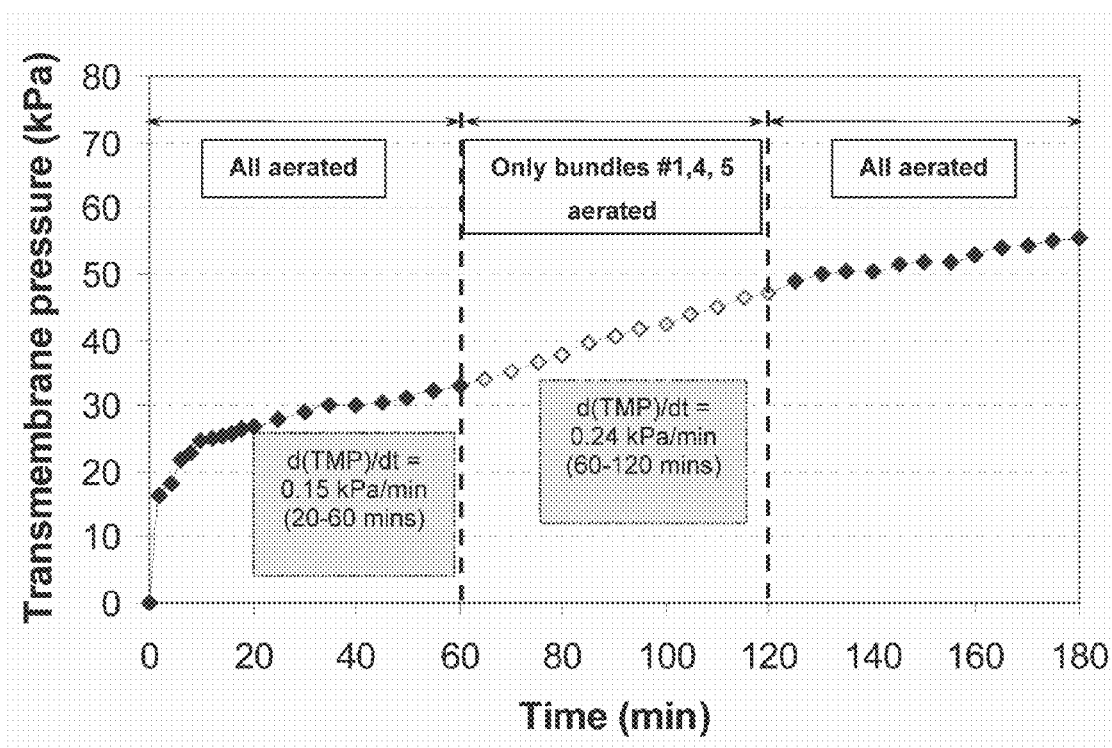
FIG. 25 illustrates the transmembrane pressure variations in the experiment of which the results are illustrated in FIG. 21.

The transmembrane pressure values of the interrupted aeration experiment are plotted in FIG. 25. Open data points indicate the recordings when the local aeration malfunction occurred. Although the transformation of transmembrane pressure does not seem to be significant, the computed d(TMP)/dt values reveal that the fouling rate increased from 0.15 kPa/min (20-60 minutes) to 0.24 kPa/min when the supply of bubbles for two membrane bundles was terminated (60-120 minutes). It should be noted that the period 0-20 minutes was not taken into account for comparing the fouling rates due to initial fouling phenomenon. Once the aeration system for bundles #2 and #3 was back in operation, the fouling rate decreased to 0.14 kPa/min indicating that air bubbles could impede the pressure build up by shearing the particle deposition on the non-aerated bundles resulting in more even flow distribution.

Figure 24:
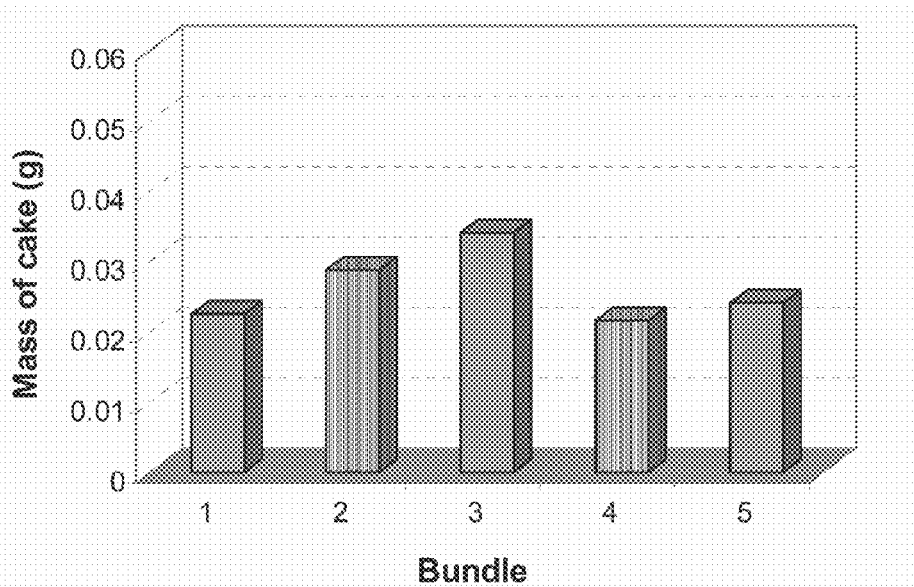
FIG. 24 illustrates the total mass of dried cake collected from each hollow fiber bundle 1 to 5 in the experiment of which the results are illustrated in FIG. 21.

It is evident that the maldistributed fluxes shown in FIGS. 14, 18, 21 and 23 by CTA sensors and the uneven fouling loads in FIGS. 15, 19 and 24 are not clearly identified by the TMP profiles in FIGS. 20 and 25. This confirms that the global TMP is unable to act as an indicator for serious localized fouling or blocking. As a result, corrective action could be delayed until the only option is to shutdown the system. To avoid this problem it was shown that localized flux measurement is feasible. The standard deviation of local fluxes provides a particularly sensitive indicator of the state of the system.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:
1. A flow distribution measuring system comprising:
 a sensor matrix adapted to measure the flow distribution of permeate passing through a membrane filtration arrangement;
 wherein said sensor matrix comprises at least two sensors measuring permeate velocity;

wherein said membrane filtration arrangement comprises at least two membrane filtration elements each comprising an outlet for said permeate;
wherein at said outlet of each of said at least two membrane filtration elements one of said sensors of said sensor matrix is located for measuring the permeate velocity at said outlet.

2. The flow distribution measuring system according to claim 1, wherein each of said sensors is located at the opposed side of said outlet.

3. The flow distribution measuring system according to claim 2, wherein each of said sensors is located opposite said outlet.

4. The flow distribution measuring system according to claim 1, wherein each of said sensors comprises a detecting surface and wherein the permeate flow exiting said outlet contacts said detecting surface in an angle between about 20 to 90°.

5. The flow distribution measuring system according to claim 1, wherein said sensor is a flat sheet sensor.

6. The flow distribution measuring system according to claim 1, wherein said sensor is a thermal anemometer sensor.

7. The flow distribution measuring system according to claim 1, wherein said membrane filtration element is selected from the group consisting of a flat sheet filtration membrane and a hollow fiber filtration membrane.

8. The flow distribution measuring system according to claim 7, wherein said membrane filtration element is a submerged flat sheet filtration membrane or a submerged hollow fiber filtration membrane.

9. The flow distribution measuring system according to claim 1, wherein the at least two membrane filtration elements are hollow fiber filtration membranes; wherein each of said hollow fiber filtration membranes comprises multiple hollow fibers each having an outlet for permeate;
wherein a sensor matrix of at least two sensors is located above said multiple outlets of each hollow fiber of said hollow fiber filtration membrane.

10. The flow distribution measuring system according to claim 1, wherein said sensor matrix is arranged in a cap which is affixed to an end of said membrane filtration arrangement.

11. The flow distribution measuring system according to claim 10, wherein said cap further comprises an outlet through which permeate from each of said at least two membrane filtration elements exits said cap.

12. The flow distribution measuring system according to claim 10, wherein said sensors of said sensor matrix are embedded in a surface of said cap facing said outlets.

13. The flow distribution measuring system according to claim 10, wherein said sensors of said sensor matrix are fixed on a surface of said cap facing said outlets.

14. The flow distribution measuring system according to claim 1, wherein said outlets are connected to an outlet tubing; wherein the inner diameter of said outlet tubing is smaller than the inner diameter of said outlets of said membrane filtration elements.

15. The flow distribution measuring system according to claim 1, wherein said sensor matrix comprises a further sensor type which measures a parameter other than the permeate velocity.

16. The flow distribution measuring system according to claim 1 comprising multiple membrane filtration arrangements.

17. A method of measuring the flow distribution in a membrane filtration arrangement comprising:
providing a flow distribution measuring system according to claim 1; and
measuring the individual permeate flow velocity at each outlet of said membrane filtration arrangement to determine the flow distribution pattern in said membrane filtration arrangement.

18. A flow distribution measuring system comprising:
a sensor matrix adapted to measure the flow distribution of permeate passing through a hollow fiber filtration membrane;
wherein said hollow fiber filtration membrane comprises multiple hollow fibers each having an outlet for permeate;
wherein said sensor matrix comprises at least two sensors measuring permeate velocity; and
wherein said at least two sensors are arranged above the multiple outlets of said multiple hollow fibers.

19. The flow distribution measuring system according to claim 18, wherein said sensor matrix is arranged in a cap which is affixed to an end of said hollow fiber filtration membrane.

20. The flow distribution measuring system according to claim 18, wherein said cap further comprises an outlet through which permeate from said hollow fiber filtration membrane exits said cap.

21. The flow distribution measuring system according to claim 18, wherein said sensor matrix comprises a further sensor type which measures a parameter other than the permeate velocity.

22. A method of measuring the flow distribution in a hollow fiber filtration membrane; comprising:
providing a flow distribution measuring system according to claim 17; and
measuring the permeate flow velocity above the outlets of the hollow fibers of the hollow fiber filtration membrane to determine the flow distribution pattern in the hollow fiber filtration membrane.

23. A cap comprising a sensor matrix which comprises sensors which are adapted to measure the velocity of permeate exiting through outlets of at least two membrane filtration elements of a membrane filtration arrangement;
wherein said cap is adapted to be affixed on a membrane filtration arrangement;
wherein said cap comprises an outlet through which said permeate can exit said cap.

24. The cap according to claim 23, wherein said sensors of said sensor matrix are embedded in a surface of said cap facing said outlets of said membrane filtration arrangement.

25. The cap according to claim 23, wherein said sensors of said sensor matrix are fixed on a surface of said cap facing said outlets of said membrane filtration arrangement.

26. The cap according to claim 23, wherein said sensors of said sensor matrix are flat sheet sensors.

27. The cap according to claim 23, wherein said sensors are thermal anemometer sensor.

28. The cap according to claim 23, wherein said cap further comprises outlet tubings adapted to be connected to outlets of a membrane filtration element; wherein the inner diameter of said outlet tubing is smaller than the inner diameter of said outlets of said membrane filtration elements.

29. The cap according to claim 23, wherein said sensor matrix comprises a further sensor type which measures a parameter other than the permeate velocity.

30. A method of measuring the flow distribution in a membrane filtration arrangement comprising:
providing a cap according to claim 23;
affixing said cap to an end of a membrane filtration arrangement, wherein said end comprises outlets of membrane filtration elements forming part of said membrane filtration arrangement;

measuring the individual permeate flow velocity at each outlet of said membrane filtration arrangement to determine the flow distribution pattern in said membrane filtration arrangement.

31. A cap comprising a sensor matrix which comprises sensors which are adapted to measure the velocity of permeate exiting through multiple outlets of hollow fibers of a hollow fiber filtration membrane;

wherein the cap is adapted to be affixed on the hollow fiber filtration membrane; and wherein the cap comprises an outlet through which the permeate exits the cap.

32. A method of measuring the flow distribution in a hollow fiber filtration membrane comprising:

providing a cap according to claim 31;

affixing said cap to an end of said hollow fiber filtration membrane, wherein said end comprises said outlets of the multiple hollow fibers comprised in said hollow fiber filtration membrane; and measuring the permeate flow velocity above the outlets of said hollow fibers of said hollow fiber filtration membrane to determine the flow distribution pattern in said hollow fiber filtration membrane.

* * * * *

UNITED STATES PATENT AND TRADEMARK OFFICE
CERTIFICATE OF CORRECTION

| | |
|---|---|
| PATENT NO. | : 8,100,005 B2 |
| APPLICATION NO. | : 12/415940 |
| DATED | : January 24, 2012 |
| INVENTOR(S) | : Anthony G. Fane et al. |

It is certified that error appears in the above-identified patent and that said Letters Patent is hereby corrected as shown below:

Column 20, Line 31:
"to claim 17; and" should read, --to claim 18; and--.

Signed and Sealed this
Tenth Day of July, 2012

David J. Kappos
*Director of the United States Patent and Trademark Office*